(12) United States Patent
Grubbs

(10) Patent No.: US 10,813,710 B2
(45) Date of Patent: Oct. 27, 2020

(54) TELEROBOTIC SURGERY SYSTEM USING MINIMALLY INVASIVE SURGICAL TOOL WITH VARIABLE FORCE SCALING AND FEEDBACK AND RELAYED COMMUNICATIONS BETWEEN REMOTE SURGEON AND SURGERY STATION

(71) Applicant: KINDHEART, INC., Chapel Hill, NC (US)

(72) Inventor: W. Andrew Grubbs, Chapel Hill, NC (US)

(73) Assignee: KINDHEART, INC., Chapel Hill, NC (US)

( * ) Notice: Subject to any disclaimer, the term of this patent is extended or adjusted under 35 U.S.C. 154(b) by 347 days.

(21) Appl. No.: 15/899,657

(22) Filed: Feb. 20, 2018

(65) Prior Publication Data

US 2018/0250086 A1    Sep. 6, 2018

Related U.S. Application Data

(60) Provisional application No. 62/466,662, filed on Mar. 3, 2017, provisional application No. 62/466,012, filed on Mar. 2, 2017.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/35* (2016.02); *A61B 34/76* (2016.02); *A61B 34/77* (2016.02);
(Continued)

(58) Field of Classification Search
CPC ....... A61B 34/25; A61B 34/285; A61B 34/32; A61B 34/35; A61B 34/37;
(Continued)

(56) References Cited

U.S. PATENT DOCUMENTS

| 5,217,003 A | 6/1993 | Wilk |
| 5,609,560 A | 3/1997 | Ichikawa et al. |

(Continued)

FOREIGN PATENT DOCUMENTS

| EP | 2070487 | 6/2009 |
| WO | 2012058533 | 5/2012 |

OTHER PUBLICATIONS

Park et al., "Patients Benefit While Surgeons Suffer: An Impending Epidemic"; Presented at the American College of Surgeons 94th Annual Clinical Congress, San Francisco, CA; Oct. 2008; Journal of the American College of Surgeons, vol. 210, No. 3, Mar. 2010; pp. 306-313.

(Continued)

*Primary Examiner* — Timothy A Musselman
(74) *Attorney, Agent, or Firm* — Allen, Dyer, Doppelt + Gilchrist, P.A.

(57) ABSTRACT

A telerobotic surgery system includes a robotic surgery station having a first pair of robot arms, each carrying a laparoscopic tool and each having a robot arm drive. A first controller is connected to each robot arm drive. Harvested animal tissue is at the robotic surgery station. A remote surgeon station includes a second pair of robot arms, each carrying a laparoscopic tool and each having a robot arm drive. A second controller receives data regarding movement of the second pair of robot arms and respective laparoscopic tool based on user manipulation of each laparoscopic tool at the remote surgeon station. A communications network couples the first and second controllers with the second (Continued)

controller operative as a master and the first controller configured to control each robot arm drive and effect one-to-one movement of the first pair of robot arms and carried laparoscopic tools as a slave.

14 Claims, 16 Drawing Sheets

(51) Int. Cl.
*A61B 34/35* (2016.01)
*G09B 23/28* (2006.01)
*A61B 34/32* (2016.01)
*A61B 34/30* (2016.01)

(52) U.S. Cl.
CPC ............ *G09B 23/285* (2013.01); *A61B 34/25* (2016.02); *A61B 34/32* (2016.02); *A61B 34/75* (2016.02); *A61B 2034/305* (2016.02)

(58) Field of Classification Search
CPC ........ A61B 34/75–77; A61B 2034/305; G09B 23/28; G09B 23/283; G09B 23/285–286
See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 6,331,181 B1 | 12/2001 | Tierney et al. | |
| 6,441,577 B2 | 8/2002 | Blumenkranz et al. | |
| 6,491,701 B2 | 12/2002 | Tierney et al. | |
| 6,659,939 B2 | 12/2003 | Moll et al. | |
| 6,817,974 B2 | 11/2004 | Cooper et al. | |
| 7,413,565 B2 | 8/2008 | Wang et al. | |
| 7,798,815 B2 | 9/2010 | Ramphal et al. | |
| 7,963,913 B2 | 6/2011 | Devengenzo et al. | |
| 8,668,702 B2 | 3/2014 | Awtar et al. | |
| 9,805,625 B2 | 10/2017 | Feins et al. | |
| 2006/0149418 A1* | 7/2006 | Anvari ................... | A61G 13/10 700/245 |
| 2006/0178559 A1 | 8/2006 | Kumar et al. | |
| 2006/0258938 A1 | 11/2006 | Hoffman et al. | |
| 2009/0246747 A1* | 10/2009 | Buckman, Jr. ....... | G09B 23/285 434/272 |
| 2010/0274087 A1 | 10/2010 | Diolaiti et al. | |
| 2012/0290134 A1 | 11/2012 | Zhao et al. | |
| 2013/0226343 A1 | 8/2013 | Baiden | |
| 2013/0330700 A1 | 12/2013 | Feins et al. | |
| 2014/0236175 A1 | 8/2014 | Cooper et al. | |
| 2014/0282196 A1 | 9/2014 | Zhao et al. | |
| 2015/0066050 A1 | 3/2015 | Jardine et al. | |
| 2015/0088158 A1 | 3/2015 | Shellenberger et al. | |
| 2016/0249992 A1 | 9/2016 | Ruiz et al. | |
| 2016/0256232 A1 | 9/2016 | Awtar et al. | |
| 2016/0303734 A1 | 10/2016 | Bowles et al. | |
| 2016/0314711 A1 | 10/2016 | Grubbs | |
| 2016/0314712 A1 | 10/2016 | Grubbs | |
| 2016/0314716 A1 | 10/2016 | Grubbs | |
| 2016/0314717 A1 | 10/2016 | Grubbs | |
| 2017/0076636 A1 | 3/2017 | Moore et al. | |
| 2017/0294146 A1 | 10/2017 | Grubbs | |

OTHER PUBLICATIONS

Prince et al., "LapaRobot"; UCLA Health System, Department of Mechanical and Aerospace Engineering; University of California; Los Angeles, CA; Sep. 13, 2011; pp. 1-20.

Author Unknown, "Telesurgical/Telementoring Laparoscopic Surgical Robot (Laparobot)"; UCLA Engineering; Mechatronics and Controls Laboratory Research Website; http://www.maclab.seas.ucla.edu/research/laparobot/; downloaded from the Internet on Feb. 27, 2017; 1 page.

Prince et al., "Robotic Surgery", RTR 2012 Poster, UCLA Department of Mechanical and Aerospace Engineering; Mechatronics and Controls Laboratory; 1 page.

Allen et al., "Laparoscopic Surgical Robot for Remote In Vivo Training"; Advanced Robotics 24 (2010); Jan. 2010; pp. 1679-1694.

Chen et al., "Robotic Surgery", Technical Forum 2014 Poster; UCLA Engineering, Henry Samueli School of Engineering and Applied Science; 1 page.

Atwar et al., "FLEXDEX(TM): A Minimally Invasive Surgical Tool with Enhanced Dexterity and Intuitive Actuation"; ASME 2009 International Design Engineering Technical Conferences and Computers and Information in Engineering Conference; Aug. 30-Sep. 2, 2009; pp. 1-11.

A. Simon Turner, "Experiences with Sheep as an Animal Model for Shoulder Surgery: Strengths and Shortcomings," Journal of Shoulder and Elbow Surgery, vol. 16, Issue 5, Supplement, Sep.-Oct. 2007, pp. 158S-163S.

La Torre et al., "Resident Training in Laparoscopic Colorectal Surgery: Role of the Porcine Model"; World J Surg. Sep. 2012; 36(9):2015-20; Abstract only—1 page.

U.S. Appl. No. 61/554,741, filed Nov. 2, 2011, entitled "Method and System for Stereo Gaze Tracking" by Wenyi et al.

* cited by examiner

TELEROBOTIC SURGERY SYSTEM USING MINIMALLY INVASIVE SURGICAL TOOL WITH VARIABLE FORCE SCALING AND FEEDBACK AND RELAYED COMMUNICATIONS BETWEEN REMOTE SURGEON AND SURGERY STATION

PRIORITY APPLICATION(S)

This application is based upon provisional application Ser. No. 62/466,662 filed Mar. 3, 2017, and based upon provisional application Ser. No. 62/466,012 filed Mar. 2, 2017, the disclosures which are hereby incorporated by reference in their entirety.

FIELD OF THE INVENTION

The invention relates generally to robotic surgery using surgical simulators on harvested animal tissue, and more particularly, this invention relates to robotic surgery performed by a surgeon in a location remote from the surgical simulator.

BACKGROUND OF THE INVENTION

Historically, surgery has been performed by making relatively large incisions in a patient to access a surgical site. More recently, robotic surgery allows a surgeon to perform procedures through relatively small incisions. The surgeon passes an endoscope through a small incision, and the endoscope includes a camera that allows the surgeon to view the patient's internal organs. Robotic procedures tend to be less traumatic, and to have shorter recovery times, than conventional surgical procedures.

Representative examples of procedures that can be performed using robotic surgery include heart surgery, lung surgery, prostate surgery, hysterectomies, joint surgery, and back surgery. Companies like Intuitive Surgical, Inc. ("Intuitive") provide robotic systems that allows surgeons to perform minimally invasive surgery, including coronary artery by-pass grafting (CABG) procedures. The procedures are performed with instruments that are inserted through small incisions in the patient's chest, and controlled by robotic arms. The surgeon controls the movement of the arms, and actuates "effectors" at the end of the arms using handles and foot pedals, which are typically coupled to electronic controllers. Recent advances allow the surgeon to use voice commands, or "line-of-sight," to control the movement of the endoscope and other robotic arms. Further, the surgeon can "feel" the force applied to the tissue, so as to better control the robotic arms.

In addition to using an endoscope to view the surgical site, the surgeon can use a laser or scalpel to cut tissue, an electrocautery device to cauterize tissue, a "grabber" to grab tissue, such as cancerous tissue, to be removed from the body, and lights to illuminate the surgical site.

Each instrument has a unique control interface for its operation, so a surgeon, or pair of surgeons, must independently operate each device. For example, a surgeon might use a first foot pedal to control an electrocautery device, a second foot pedal to operate a robotic arm, and another interface to operate a laser. The handles and a screen are typically integrated into a console operated by the surgeon to control the various robotic arms and medical instruments.

It typically requires a certain amount of time to train surgeons to use these robotic systems, where an experienced surgeon might train one or more junior surgeons while performing surgery on a living patient.

U.S. Pat. No. 5,217,003 to Wilk discloses a surgical system which allows a surgeon to remotely operate robotically controlled medical instruments through a telecommunication link. However, a limitation of the Wilk system is that it only allows for one surgeon to operate the robotic arms at a given time.

U.S. Pat. No. 5,609,560 to Ichikawa et al. discloses a system that allows an operator to control a plurality of different medical devices through a single interface, though this system does not allow multiple surgeons to simultaneously perform a surgical procedure.

More recently, U.S. Pat. No. 7,413,565 to Wang discloses system that allows a senior surgeon to teach a junior surgeon how to use a robotically controlled medical instrument. Like a vehicle used to train young drivers, this system allows for both surgeons to independently control instruments by using their hand movements to move a handle, while allowing the senior surgeon to provide "force feedback," and move the junior surgeon's hand to correspond with the senior surgeon's handle movement. In this manner, the senior surgeon can guide the junior surgeon's hands through force feedback of the handles, to teach the surgeon how to use the system.

This technology is potentially useful if all of the surgeons are in the same room as the living patient. However, unless the surgeons are all in the same room as the living patient, it is unlikely that governmental rules and regulations will allow such "remote" surgical training.

Still, as it is not always convenient to have senior surgeons and junior surgeons all be in the same physical location, it would be advantageous to provide a system and method to allow for remote training in robotic surgical operations. It would also be desirable to provide a more inexpensive training technique without having to use expensive robotic systems as described above, while also permitting manually operated laparoscopic tools that provide ease in manual use and a virtual center (VC) to simulate more expensive robotic systems.

One possible solution is a laparoscopic surgical robot system having a master controller station and slave robot station with the functionality as described in the article published by Allen et al. in Advanced Robotics, January 2010 and entitled, "Laparoscopic Surgical Robot For Remote In Vivo Training," the article which is hereby incorporated by reference in its entirety. That robotic system is also described as the Laparobot and was designed by the University of California at Los Angeles (UCLA). This robotic training system includes a master control (or surgeon) station and a slave robot station, each having robot arms carrying a laparoscopic tool that operate similar to the robotic arms on more expensive machines. Each robot arm and laparoscopic tool have at least one motor/encoder attached for operation and/or movement in different degrees of freedom. For example, if a tool at the master control station has a pistol grip that controls the opening and closing of cutting jaws at the end effector, then at least one motor/encoder is attached to a similar laparoscopic tool and robot arm carried at the slave robot station and "squeezes" the trigger of that pistol grip. Another motor/encoder may rotate the tool along its long axis. If the tool has a "wrist," another motor/encoder drives that degree of freedom movement. The robot arms or manipulators detect and replicate the position of the laparoscopic tool in the "cone" of motion above the entry point into the abdominal or chest wall. The robot arms and laparoscopic tools at the surgeon or master control station will have motors/encoders and controllers to send data to motors/encoders at the robot arms and laparoscopic tools located at the surgical "slave" robot station. In one example, this master/slave robot system uses standard 5 mm diameter Karl Storz instrument housings for the robot arms such as the CLICK' line handle system.

This master/slave robotic system may operate in a tele-surgery/telemonitoring mode where the remote slave robot station replicates the motion of the tools at the master control station. The user of the master control station can freely manipulate the laparoscopic tools at the master control station in all degrees of freedom and these motions are mimicked at the slave robot station. A student may be trained on laparoscopic tasks by holding onto the tools and feeling the motions directed by the master surgeon if a student is located at the slave robot station and a master surgeon at the master control station. The student sees the same video stream as the master surgeon.

In a box-trainer mode, either the master control station or slave robot station is used as a stand-alone station and the user manipulates the tool located at the respective station to perform box trainer tasks, including peg transfers, suturing or circle cuts. In a cooperative mode, the master and slave users interact with each other through position-position base control and the operator at the master control station and the operator at the slave robot station operate their respective laparoscopic tools using position based feedback. The tool located at the master control station may follow the reference trajectory generated by the tool located at the slave robot station and the tool at the slave robot station may follow the reference trajectory generated by the tool at the master control station. It is possible to tune the dominance of the controllers and adjust the dominance of the master-slave cooperation. Thus a two-way forced feedback between the master tool and slave tool is possible. An example is when a master surgeon is at the master control station and a student is at the slave robot station and the student feels the motion of the master manipulating the controls at the master control station. Thus the student learns by following the master's movements.

In an example operation of this master/slave robotic system, a tool may be grasped by a surgeon or other operator at the master control station and the "trigger" pulled or other tool manipulation made. A motor/encoder notes the movement and the controller of the master control station sends data via the internet to the controller at the slave robot station indicating its trigger should be "pulled" at the same rate and in the same position. When the laparoscopic tool encounters resistance as the action proceeds at the slave robot station, the back-electromotive force (back-EMF) is calculated as a haptic signal and sent back to the master controller and to its motor/encoder while the master control station trigger is activated to provide as perfect as possible a replica of the haptic "push back" that the surgeon would feel if the surgeon at the master control station were actually manipulating tissue or bone. Although there is some feedback as described, there is no technique to modulate this haptic feedback to increase or decrease its effect such as if tough bone or cartilage is encountered or soft flesh.

Another drawback of laparoscopic surgery is that laparoscopic surgeons sometimes suffer repetitive motion injuries from operating their laparoscopic tools over long surgeries and when confronted with tough tissue, cartilage or bone such as described in the article entitled, "Patients Benefit While Surgeons Suffer: An Impending Epidemic" as published in the Journal of the American College of Surgeons, March 2010, the disclosure which is hereby incorporated by reference in its entirety.

SUMMARY OF THE INVENTION

This summary is provided to introduce a selection of concepts that are further described below in the Detailed Description. This summary is not intended to identify key or essential features of the claimed subject matter, nor is it intended to be used as an aid in limiting the scope of the claimed subject matter.

A telerobotic surgery system for remote surgeon training comprises a robotic surgery station having a first pair of robot arms, each carrying a laparoscopic tool and each having a robot arm drive. A first controller is connected to each robot arm drive and controls movement of the pair of robot arms and respective laparoscopic tool. Harvested animal tissue is at the robotic surgery station.

A remote surgeon station has a second pair of robot arms, each carrying a laparoscopic tool and each having a robot arm drive. A second controller is connected to each robot arm drive at the remote surgeon station and receives data regarding movement of the second pair of robot arms and respective laparoscopic tool based on user manipulation of each laparoscopic tool at the remote surgeon station. A communications network couples first and second controllers. The second controller at the robotic surgery station is operative as a master to communicate data to the first controller regarding user manipulation of the second pair of robot arms and respective laparoscopic tool. The first controller is configured to control each robot arm drive and effect one-to-one movement of the first pair of robot arms and carried laparoscopic tools as a slave based on user manipulation of each laparoscopic tool at the remote surgeon station.

In an example, the first and second controllers may each include a force feedback module to provide haptic feedback to a user at the laparoscopic tool being manipulated. The first and second controllers may each include a variable force scaling module configured to modulate the haptic feedback to a user and increase or decrease the effective tool movement force felt by the user at the laparoscopic tool being manipulated. A left turret and right turret may be positioned at each of the robotic surgery station and remote surgeon station. Each left and right turret supports a plurality of robot arms, each robot arm having a laparoscopic tool and each having a robot arm drive and connected to the respective controller at the respective station. The laparoscopic tools match in one to one correspondence with each other at the robotic surgery station and remote surgeon station and the laparoscopic tools are selectable via rotation of the turret based on surgery requirements. The second controller may be operative to effect movement of the second pair of robot arms and respective laparoscopic tools based on movement of said first pair of robot arms and laparoscopic tools. The robotic surgery station may include at least one camera, wherein the harvested animal tissue is viewable by the at least one camera so that said at least one camera generates an actual animal tissue image. The remote surgeon station may comprise at least one surgeon display cooperating with said at least one camera to display the actual animal tissue image.

In yet another example, at least one animating device is coupled to the harvested animal tissue. The at least one animating device may simulate at least one of breathing, heartbeat, and blood perfusion. The robotic surgery station may be at a first location in a first structure at a first geographic point and the remote surgeon station may be at a second location in a second structure at a second geographic point remote from the first geographic point.

In yet another example, a telerobotic surgery system for remote surgeon training comprises a robotic surgery station at a first location in a first structure at a first geographic point and includes a first pair of robot arms, each carrying a laparoscopic tool and each having a robot arm drive, and a first controller connected to each robot arm drive and controlling movement of the pair of robot arms and respective laparoscopic tool. Harvested animated animal tissue is at the robotic surgery station and comprises harvested animal tissue and at least one animating device coupled thereto.

A remote surgeon station is at a second location in a second structure at a second geographic point and includes a second pair of robot arms, each carrying a laparoscopic tool and each having a robot arm drive. A second controller is connected to each robot arm drive at the remote surgeon station and receives data regarding movement of the second pair of robot arms and respective laparoscopic tool based on user manipulation of each laparoscopic tool at the remote surgeon station.

A communications network couples first and second controllers. The second controller at the robotic surgery station is operative as a master to communicate data to the first controller regarding user manipulation of the second pair of robot arms and respective laparoscopic tool. The first controller is configured to control each robot arm drive and effect one-to-one movement of the first pair of robot arms and carried laparoscopic tools as a slave based on user manipulation of each laparoscopic tool at the remote surgeon station.

DESCRIPTION OF THE DRAWINGS

Other objects, features and advantages of the present invention will become apparent from the detailed description of the invention which follows, when considered in light of the accompanying drawings in which.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1:
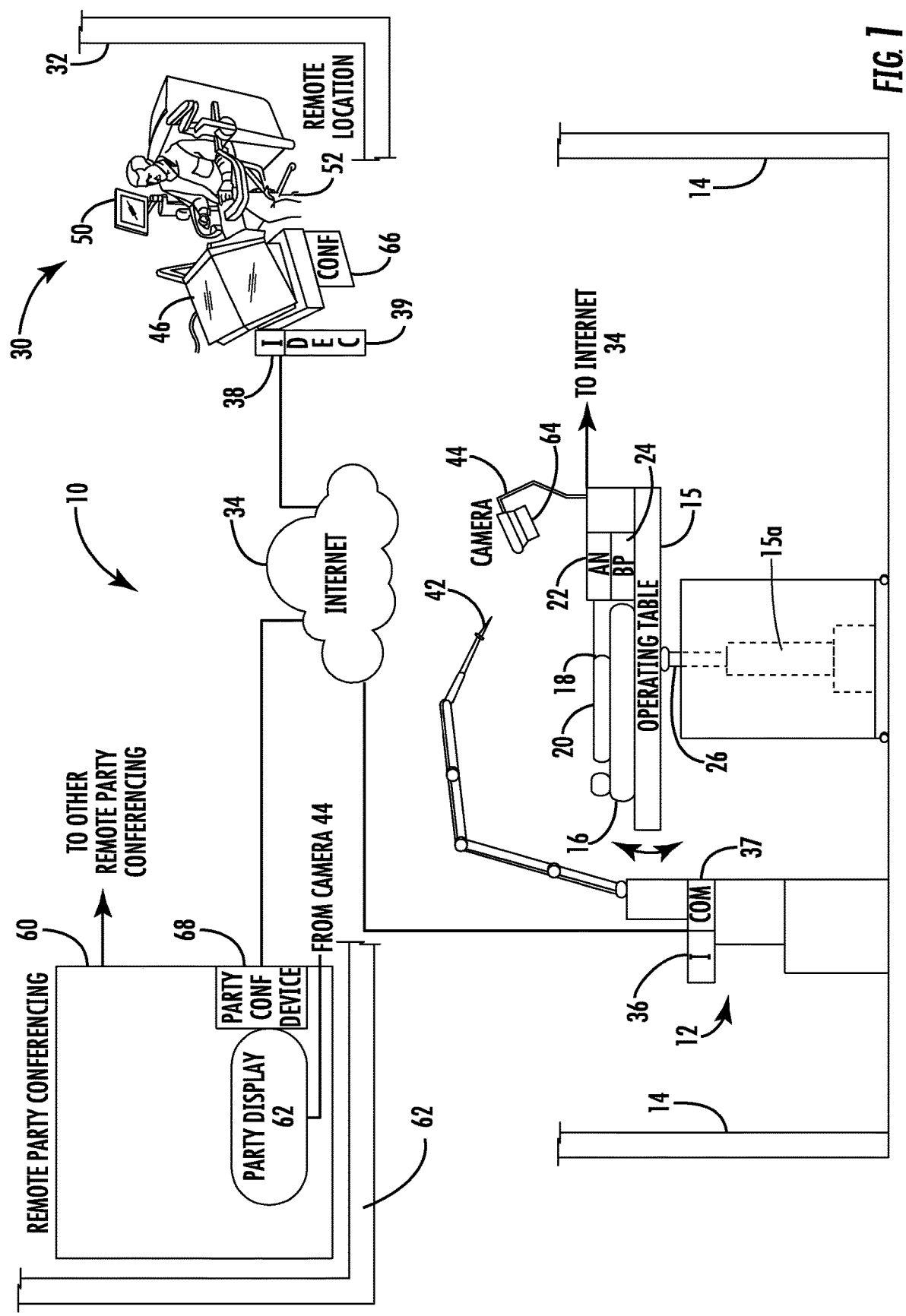
FIG. 1 is a fragmentary, block diagram of the telerobotic surgery system showing basic features in accordance with a non-limiting example.

The telerobotics surgery system for remote surgeon training is shown generally at 10 in FIG. 1 and includes a robotic surgery station 12 at a first location in a first structure 14 at a first geographic point. The first structure 14 could be a fixed building or could be a vehicle/trailer or other structure temporarily positioned for use. The robotic surgery station 12 simulates a patient undergoing robotic surgery. It includes an operating table shown generally at 15, and in this example, a mannequin 16 includes an animal tissue cassette 18 and is mounted on the operating table 14. The cassette 18 is configured to hold at least harvested animal tissue 20. At least one animating device 22 is coupled thereto. A blood perfusion device 24 is coupled to the harvested animal tissue 20, e.g., lung tissue and heart tissue in this example. In a preferred example, the harvested animal tissue 20 does not include human cadaver tissue. While porcine tissue is used for many training scenarios, the tissue of sheep, goat or canine may be used as well. The animating device 22 is a movement device that is configured to simulate normal and abnormal breathing, and normal and abnormal heartbeat using techniques such as balloons inserted into the tissue as explained below. As noted before, the mannequin 16 may receive the tissue cassette 18 that may be tilted or moved using an actuator 26.

A remote surgeon station 30 is at a second location in a second structure 32 at a second geographic point that is remote from the first geographic point. A communications network 34, such as the Internet, couples the robotic surgery station 12 and the remote surgeon station 30 so that a surgeon at the remote surgeon station is able to remotely train using the harvested animated animal 20 tissue at the robotic surgery station. In the example, the communications network 34 may have a latency of not greater than 200 milliseconds, and in another example, may have a latency of not greater than 140 milliseconds. As illustrated, a first communications interface 36 is coupled to the robotic surgery station 12 and a second communications interface 38 is coupled to the remote surgeon station 30. The first and second communications interfaces 36, 38 are configured to be coupled together via the internet as the communications network 34 in this example. As illustrated, the robotic surgery station 12 is positioned adjacent the operating table 15 and has at least one surgical tool 42, which could be different tools depending on what type of surgery is simulated. At least one camera 44 is located at the robotic surgery station 12 and the remote surgeon station 30 includes at least one display 46 coupled to the at least one camera 44 via the communications network 34, in this case the internet. In an example, the first communications interface 36 is configured to determine if a latency is above a threshold, and when above a threshold, performs at least one of image size reduction and reducing the peripheral image resolution on the display 46. This will allow data to be transported over the internet connection while maintaining high image resolution at those areas of the image that are more critical for the training.

The first communications interface 36 may include a data compression device 37 and the second communications interface 38 may include a data decompression device 39. In an example, the at least one camera 44 may be formed as a stereo image camera and the at least one display 46 may include a binocular display 50 as illustrated in FIG. 1 that could be moved directly over the eyes of the trainee. Alternatively, the trainee could view the large display screen 46 or manipulate the binocular display 50 and view the surgical procedure.

As noted before, the at least one animating device 22 may include a movement animating device to simulate at least one of the breathing and heartbeat, including normal and abnormal breathing, and normal and abnormal heartbeat.

In an example, the first location having the robotic surgery station 12 may be associated with a room not for live human operations. The second location having the remote surgeon station 30 may be associated with an operating room for live human operations in one example. The trainee such as a student surgeon or experienced surgeon learning new techniques may sit in the operator chair that is part of a real operating room and operate the robotic surgery station 12 telerobotically as described in greater detail below. As noted before, the remote surgeon station 30 includes at least one input device 52 as hand controls in this example, and the robotic surgery station includes at least one output device coupled to the at least one manual input device 52, which in this example is the at least one robotic surgical tool 42 as illustrated that provides a feedback signal with the at least one manual input device shown as the hand controls and responsive to the feedback signal.

As illustrated in FIG. 1, a remote party conferencing station 60 is at a third location in a third structure 62 at a third geographic point remote from the first and second geographic points. The communications network 34 such as the internet not only couples the robotic surgery station 12 to the remote surgeon station 30, but also couples to the remote party conferencing station 60 so that a surgeon at the remote surgeon station 30 is able to remotely train using the harvested animal tissue 20 at the robotic surgery station 12, and while conferencing with a party at the remote party conferencing station 60. For example, there could be a group of surgeons or students located at the remote party conferencing station that will observe, watch and even confer with the surgeon or student trainee located at the remote surgery station. There can be multiple stations and multiple persons present at each station. The remote party conferencing station 60 may also include at least one party display 62 coupled to the at least one camera 44 located at the robotic surgery station 12 via the communications network 34. A video recorder 64 may be coupled to the at least one camera 44. The remote surgeon station 30 may include a surgeon conferencing device 66 and the remote party conferencing station 60 may including a party conferencing device 68 coupled to the surgeon conferencing device via the communications network 34. Thus, a voice conference may be established between the surgeon at the surgeon conferencing device 66 located at the remote surgeon station 30 and the party conferencing device 68 located at the remote party conferencing station 60.

Figure 2:
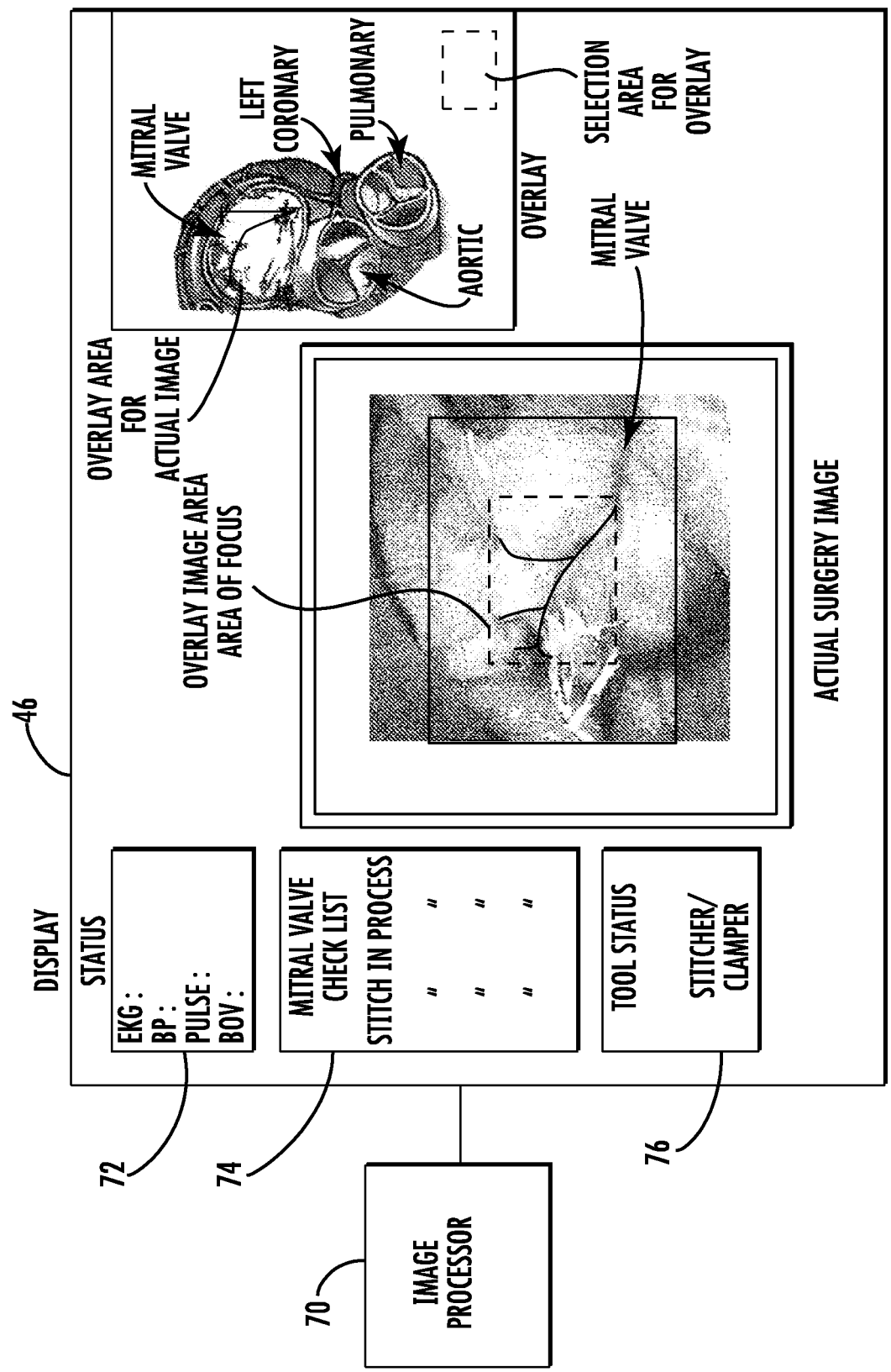
FIG. 2 is a block diagram of an image processor that generates an additional image on the at least one surgeon display in accordance with a non-limiting example.

At the remote surgeon station 30, an image processor 70 may generate an additional image on the at least one surgeon display 46 and the additional image may include an anatomical structure image corresponding to the actual animal tissue image such as shown in FIG. 2. This image processor 70 may be configured to overlay the anatomical structure image on the actual animal tissue image. For example, the additional image may include a surgery status information image 72, for example, a training scenario. The surgery status information image 72 may include at least one of an EKG value, a blood pressure value, a heart rate value, and a blood oxygen value and be synchronized to the actual animal tissue image. The additional image may also include a surgery instructional image 74, for example, a surgery checklist. For example, the harvested animal tissue may simulate a desired heartbeat, for example, 78 bpm, and the tissue, if cut, will bleed and the heartbeat will be displayed and recorded. The "corresponding" anatomical image added on the surgeon display could be the heart and lung image or heart image 76 of a person such as from Grey's Anatomy, for example. The surgical status information could be an indication such as the color change for the robotic tool, or color change to indicate operation of a cautery tool or activation of a stapler. This all helps in training the surgeon or student surgeon.

The operating table 15 could include an immersion tank carried by the operating table and configured to contain liquid. An inflator could be configured to be coupled to harvested animal lung tissue to inflate lung tissue and be connected to a heart tissue via inflatable balloons and pulsed to form a heartbeat as explained below. The operating table could include a lift mechanism 15a to move the animal tissue cassette and/or mannequin between different operating positions.

Examples of simulated surgical procedures include heart by-pass operations, valve replacements or repair, lung re-sectioning, tumor removal, prostatectomy, appendectomy, hernia operations, stomach stapling/lap band operations, orthopedic surgery, such as rotator cuff repair and arthroscopic knee surgery. In addition to actual operations, specific skill sets can be developed, for example, vein dissection, use of staplers, cautery, and the like. Each of these surgeries and/or skill sets can be practiced using an appropriate tissue, organ or organ block, as discussed in detail below.

The systems include one or more surgical simulator units that include animal, cadaver, or artificial tissues, organs, or organ systems, providing a non-living but realistic platform on which to perform surgery. The systems also include one or more instruments for performing robotic surgery, so that one or more simulated surgical procedures can be performed on tissues, organs, or organ systems in the surgical simulator units. The systems optionally, but preferably, also include a telecommunications system which allows remote access to, and control of, the instruments used to perform robotic surgery, thus allowing simulated robotic surgery to be performed remotely.

In one aspect of this embodiment, a surgeon can remotely access a simulation center, and either perform an operation or practice their skills. The simulation center includes one or more surgical simulators, one or more instruments for robotic surgery and animated animal tissue such as part of a cassette or mannequin.

In another aspect of this embodiment, a teaching surgeon can remotely access a surgical simulation center that includes the systems described herein, and instruct a student surgeon on how to perform a particular robotic surgical operation. The student surgeon can either be present at the simulation center, or can remotely access the simulation center. The teaching surgeon can perform one or more of the following:

a) teach the procedure as the student observes, b) observe the student as the student performs the procedure, and give feedback, which can include real-time feedback and/or feedback after the procedure is completed, and c) allow the student to perform the procedure, but take over control of the instruments where the student, for example, where the instructor perceives that the student has made a mistake, optionally by providing tactile feedback to the student, so that the student "feels" how the proper motion of the surgical instruments should be.

In still another aspect of this embodiment, multiple surgeons can access a simulation center, with each surgeon individually accessing the center locally or remotely. A plurality of surgical simulators, each of which includes its own tissue, organ, or organ block "cassettes," and each of which is controlled by a different robot. In this embodiment, a single instructor can guide a plurality of students through a surgery or skills exercise.

Where more than one surgeon is operating a robotic instrument, the instructor and/or students can be joined in a virtual surgical setting using appropriate web conferencing software, such as that provided by Adobe Connect.

By using web conferencing software, one can provide access across devices, and allow sessions to be recorded and, optionally, edited at a later time. Web conferencing can provide highly secure communications, and can also ensure compliance with applicable laws. The conference can provide an immersive experience for the students, and allows for them to easily create a record of their attendance. Each surgical simulation can be customized, and different types of content can be delivered. For example, an instructor can alternate between a visual slide presentation and/or video presentation of the type of surgical procedure to be performed, and the performance of the actual procedure in real-time. The web conference can allow for mobile learning across multiple devices, and allow some students to participate live, and others to participate later in an "on-demand" manner. As a result, a web conference can provide efficient management and tracking for training on surgical simulators.

In one aspect of this embodiment, cloud computing is used to control the robotic surgical instruments, where one or more surgeons can participate in the surgical procedure. For example, one surgeon can teach other surgeons how to perform the procedure, and/or multiple surgeons can work collaboratively on a single "patient" to perform one or more procedures.

The individual elements of the systems described herein are described in detail below.

I. Types of Tissue/Organs

The surgical simulator systems includes animal, cadaver human, or artificial tissue and/or organs, and/or organ blocks including the organs, or combinations thereof. These tissues, organs, and/or organ blocks are included in simulated surgical devices, such that a surgeon can perform lifelike surgery on real, or at least realistic, tissue.

One or more of these tissue, organs, and/or organ blocks can be hooked up to a source of animal blood, theater blood, or other colored liquid to simulate bleeding, and/or can be hooked up to a source of a gas and/or vacuum, which can be used to simulate organ movement.

For example, animal lungs present in the surgical simulator can be expanded and contracted to simulate normal breathing, or to simulate other types of breathing, such as shallow breathing, coughing, and the like. A heart can be expanded and contracted to simulate a heartbeat, for example, by inflating one or more balloons inside the heart, for example, inside the ventricles.

So as to allow connection to a source of a gas or vacuum (to inflate/deflate the lung or cause the heart to "beat"), or to artificial or animal blood, the organs can be equipped with quick-connect tubes. Using these quick-connect tubes, the organs or organ blocks can be quickly incorporated into a surgical simulator, and attached to a source of air and vacuum, such as a bellows, an ambu bag, and the like. Where the surgical simulator includes a heart, the heart can be expanded and contracted, for example, using a balloon attached to a source of air and a source of vacuum.

Though judicious application of a gas to a balloon or other expandable member, different heartbeat rhythms can be produced, simulating a normal heartbeat, a distressed heartbeat, arrhythmias, a heart attack, and the like. In one aspect of this embodiment, a surgeon can simulate the steps needed to be taken following a myocardial infarction, where the surgical instruments must often be removed before resuscitation efforts can be initiated.

The surgical simulator can also include animal joints that simulate human joints, so that joint surgery can be simulated. For example, sheep and goats are a convenient large-animal model for rotator cuff repair (Turner, "Experiences with Sheep as an Animal Model for Shoulder Surgery: Strengths and shortcomings," Journal of Shoulder and Elbow Surgery, Volume 16, Issue 5, Supplement, September-October 2007, Pages 5158-S163). Tenotomy of the infraspinatus tendon and subsequent reattachment to the proximal humerus is useful to address the biomechanical, histologic, and biochemical processes of rotator cuff repair. Detaching this tendon and immediately reattaching it does not represent the clinical picture but serves as a relatively rapid way to screen different suture anchors, suture patterns, scaffolds, and other treatments. A porcine model can be used to simulate knee surgery. For example, anatomic ACL reconstructions and other types of knee surgeries can be simulated using a porcine model.

Laparoscopic colorectal surgery (LCRS) is an effective option for the treatment of various colorectal conditions, and can be evaluated in an animal porcine model (La Torre and Caruso, "Resident training in laparoscopic colorectal surgery: role of the porcine model." World J Surg. 2012 September; 36(9):2015-20).

Non-limiting examples of animals from which the tissue, organ, and organ blocks can be obtained include cow, sheep, goat, pig, baboon, dog, and cat.

Development of a Module Lot

A group of animal tissue collections may be made from a series of animals before butchering for food so that no animals are sacrificed beyond what would be butchered for food. By collecting a series of tissue collections by the same facility using the same procedure from the same herd of animals (same breed, same age, same food), there will be extensive similarities among the collected tissue samples. As is understood by those of skill in art, some features vary even between identical twins such as the vascular pattern around the exterior of the heart so some features cannot be closely controlled. However, certain degrees of variability can be decreased by clustering tissue samples by gender of donor animal, nominal weight of donor animal, or some other property of the animal or classification made of the harvested tissue sample.

The organs used in the surgical simulators can be preselected so as to have various defects, such as tumors, valve defects, arterial blockages, and the like, or can be selected to be as close to identical as possible. In the former embodiment, a surgeon can demonstrate a particular type of operation where a particular defect is present, and in the latter embodiment, a surgical instructor can demonstrate a technique to multiple students, using organs that are closely matched, so that the results would be expected to be the same if the students perform the surgery correctly.

In general, the organs may be characterized using a wide variety of available metrics. These may include volume of ventricles, stiffness of the muscle tissue (restitution test), specific gravity, % fat, pressure testing, presence or absence of tumors, blockage or arteries, etc. The recorded metrics will be specific to the scenario being replicated. Ideally, the organs selected are as close to the size and weight of human organs.

Examples of classification of the tissue samples may include:

A) Some characterization of the amount of fatty material surrounding the tissue of interest.

B) Some characterization of the pliability/stiffness of the tissue.

C) Some characterization of the properties of the relevant blood vessels such as degree of occlusion.

D) One way to characterize an organ is the time it takes for a fluid to drip out from a container and into an organ. As the receiving volume of the organ will be relatively uniform (for organs of the same size) this may characterize the ability of fluids to flow through the structures in the organ and out.

Representative Xenographic Organ Preparation

Porcine organ blocks including the heart with pericardium, lungs, trachea, esophagus, and 8-12 inches of aorta can be obtained from a local supplier. There is no need to sacrifice animals to obtain these organs or organ blocks, as these can be harvested from an animal before butchering the animal for food products.

Organ preparation can begin with an incision of the pericardium on the right posterior side of the heart, so it can later be reattached with no noticeable holes when viewed from the left side. The superior vena cava, inferior vena cava, right pulmonary artery, and right pulmonary veins can then be divided with care taken to leave as much vessel length as possible. After the right lung is fully detached, the organs can be washed extensively to remove coagulated blood from the heart and vessels. All divided vessels, except for the main branch of the right pulmonary artery and right superior pulmonary vein, can be tied off, for example, using 0-silk.

As an example of quick-connect tubes, small diameter plastic tubes with Luer-Lok® connectors can then be placed into the divided right pulmonary artery and right superior pulmonary vein, and fixed in place, for example, using purse-string sutures. To create distention of the aorta, one can inject silicone caulking to the level of the ascending aorta.

After the silicone cures, the brachiocephalic trunk and left common carotid can be tied off, for example, using 0-silk.

The left main stem bronchus can be occluded, for example, by stapling the divided right main stem bronchus as well as the proximal trachea. The left hilum can remain unaltered, and all modifications to the heart can be hidden by the pericardium during the procedure.

Following preparation, the organs can be stored at a relatively low temperature, for example, 4 degrees Celsius, in an alcoholic solution, for example, 10% ethanol containing teaspoon of red food coloring. In this manner, the organs typically remain fresh for at least 1 month. Use of higher concentrations of alcohol, such as 40% ethanol, can preserve the organs for over a year, and, ideally, up to 18 months, and can perform as well as freshly-harvested organs.

Simulating Trauma

While having similar tissue for use in creating various staged reality modules within a lot is helpful, the ability to precisely create trauma in ex vivo tissue samples is of even greater importance. Having harvested tissue samples of a similar size and quality allows the tissue samples to be placed in a jig so that the trauma may be applied in a controlled way a precise offset from one or more anatomic markers. Examples of trauma include:

A) A set of uniform metal pieces may be created and implanted a set depth in a set location to allow for a set of shrapnel wounds to be placed in a series of tissue samples that will become staged reality modules within a given lot.

B) A particular volume of silicon or some analogous material may be placed in the same location in a series of harvested lungs to emulate lung tumors.

C) Trauma may be emulated for chemical burns or other trauma to the outer layers of tissue of a faux patient.

D) In lieu of implanting faux ballistic debris, organs placed in jigs can receive ballistic projectiles from a weapon.

In order to verify that the trauma induced fits within the parameters for this particular set of traumatized organs, the trauma could be examined and characterized by ultrasound or some other diagnostic imaging method. One may also sprinkle a little gunpowder around the wound just before the session started and ignite it to create fresh burns and realistic smells of the battlefield.

Spleen Example

Another example of a staged reality module is a spleen that has received a standardized shrapnel injury (precise and repeatable insertion of standardized pieces of metal rather than actual pieces of shrapnel from an explosion). The staged reality module for the injured spleen can be placed as module A-50 (Figure A). The staged reality module would be prepared with quick connect fittings to allow connection to a port on an umbilical cable to provide a source of faux blood and to provide a clear liquid to weep from the wound.

Optionally, the spleen may have instrumentation to provide an indication of when the spleen was first by cut the surgeon. This information could be conveyed by the data bus. In order to provide a standardized set of injured spleens for testing or simply for use in an ordered curriculum, a set of substantially identical spleens harvested from donor animals that will be butchered for food may be prepared in the substantially same way.

As noted above, the packaging may convey information about the staged reality spleen module.

A porcine organ block can be placed in a lower tray to retain fluids analogous to a metal baking tray. For purposes of simulating a human, the porcine heart can be rotated to emulate the position of a human heart in a torso. For example, the left side of the porcine heart can be placed into the tray with the left lung placed over an inflatable air bladder.

Adapting Organs for Inflation/Deflation, Beating, and/or Bleeding

Inflation and deflation of lungs of a real patient causes the rise and fall of the mediastinum. An appropriate volume of air or some other fluid may be used to inflate and deflate an appropriately sized and placed container hidden under the tissue to be animated with movement. For example a respiration rate of 20 breaths per minute can be simulated by periodically expanding an air bladder such as a whoopee cushion, or an empty one-liter IV bag that is folded in half.

Lightly pressurized theater blood or animal blood can be provided through a connection to the umbilical cable port to provide blood emulating fluid into the divided right pulmonary artery and divided right superior pulmonary vein to distend and pressurize the venous and arterial systems. Static fluid pressure within the vessels can be achieved using gravity flow from an IV bag. Pressure is ideally limited, to avoid severe pulmonary edema. Extended perfusion times (1-2 hours) can be maintained without substantial fluid leakage into the airways by preparing the porcine organ block to occlude the left mainstem bronchus to inhibit leaking and loss of pressure.

A balloon placed in the heart and connected to a closed system air source to allow for emulating the beating of a heart (such as at a rate of 78 beats per minute) adds to the sense of realism of the simulated surgical procedure. In this manner, the organs and/or organ blocks can be animated by providing one quick connect fitting to connect the heart balloon to an air supply to provide a beating heart effect, and a second quick connect fitting can be connected to a different pneumatic connection to provide air to the lungs, providing lung movement to simulate breathing. A fluid quick connect fitting connected to the joined blood vessels can allow for slightly pressured simulated blood to be provided. One or more of these connections can be made to an umbilical cable.

As used in this specification, a quick connect fitting is one that may be connected to a corresponding fitting without using tools. A quick connect fitting can be used to connect to hydraulic line, pneumatic line, electrical line, and/or digital communication bus.

II. Surgical Simulator

The tissue, organs, and/or organ blocks described above are included in a carrier/container to simulate the view a surgeon would see when performing surgery. This view may simply include draping over the tissue, organs, or organ blocks to be operated on, where the organs are stored in a box or other suitable container, held at the height appropriate for the surgeon to perform the surgery. However, in some embodiments, the tissue, organs, and/or organ blocks described above are included in a mannequin, and/or are provided along with photographs representative of what would be seen in an actual human undergoing this surgical procedure, so as to provide a more realistic surgical experience.

Modules including the tissue, organs, and/or organ blocks, along with the quick connections to sources of gas, vacuum, and/or animal or fake blood, can be quickly inserted into a relevant portion of a segmented mannequin, connected via one or more quick connect fittings to corresponding fittings on a convenient umbilical cable port to quickly prepare a mannequin for simulated robotic surgery.

Other staged reality modules may be likewise connected. Pressure levels (such as the height of an IV bag supplying the master-controller) or pulse volumes (for heart or lung motion) may be adjusted at the master-controller. The mannequin may then be draped to expose the relevant surgical sites. Optionally, the packaging carrying the staged reality module (the porcine organ block with modifications and quick connect fittings) may include a bar code, data matrix code, other optical code, or other machine readable data storage device that is accessed by a bar code reader or other reader device in data communication with the master-controller. Thus data concerning this specific staged reality module can be made available to the master-controller and combined with other information gathered during the surgical simulation and made part of a data record for this training or certification session. Another option would be the use of a passive RFID label.

Figure 3:
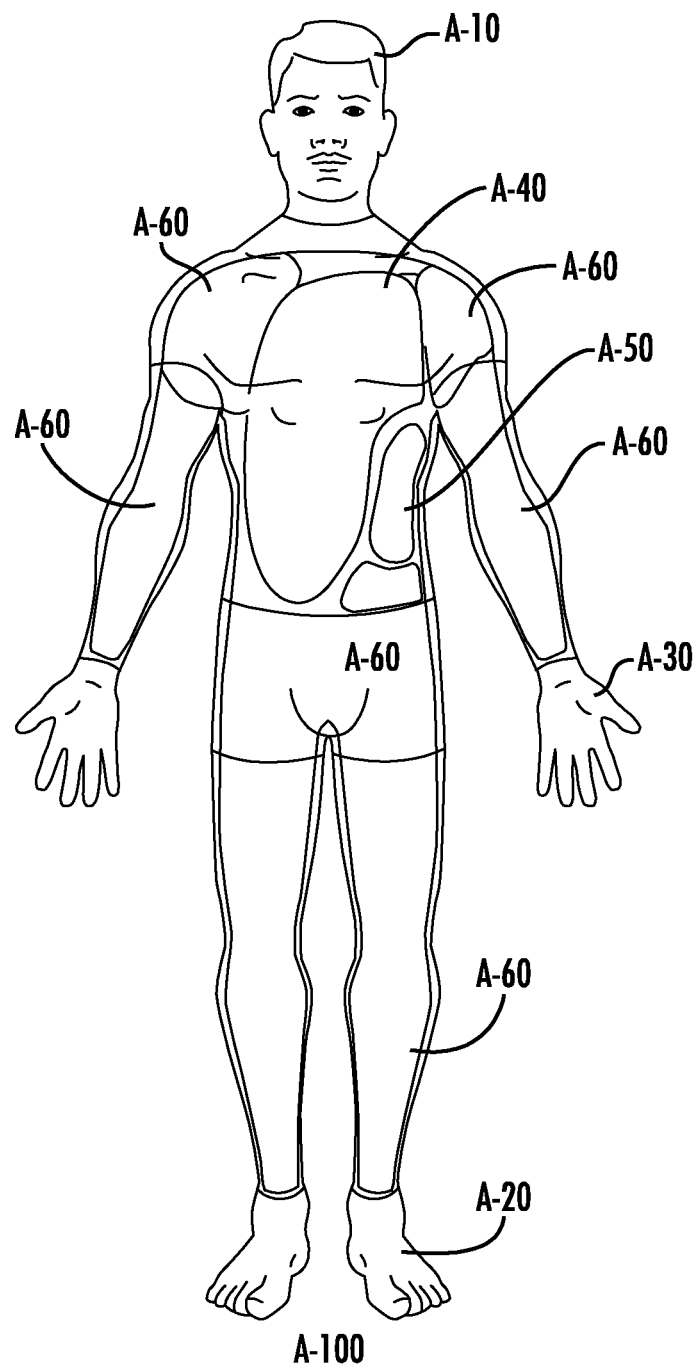
FIG. 3 is a top view of a segmented mannequin A-100. The mannequin may include certain permanent features such as a mannequin head A-10, mannequin feet A-20, mannequin hands A-30 that may be used in accordance with a non-limiting example.

Although other embodiments can be used, in one embodiment, the surgical simulator includes a segmented mannequin, as shown in FIG. 3. FIG. 3 is a top view of a segmented mannequin A-100. The mannequin may include certain permanent features such as a mannequin head A-10, mannequin feet A-20, mannequin hands A-30. These permanent features may be made of a material that roughly approximates the feel and weight of a human component although without the need to emulate the properties of tissue when cut or sewn. These components could be obtained from sources that provide mannequin parts for mannequins used for CPR practice. The permanent mannequin parts used away from the surgical sites are there to assist in the perception in the staged reality that the patient is a living person. Alternatively, preserved parts from a cadaver may be used. In other alternatives, these body portions that are not directly involved with a staged reality of an event requiring surgery may be omitted and covered with drapes.

Staged reality component A-40 may be some subset of the mediastinum. For example, A-40 may represent a heart and pair of lungs. A separate staged reality module present in FIG. 3 is a spleen module shown as A-50. Note that while this example shows two active staged reality modules, in many training exercises, a single staged reality module will be presented with a number of repetitions.

The remainder of the segmented mannequin A-100 may be filled with a series of mannequin filler pieces A-60. The filler pieces may be made of ballistic gelatin. Ballistic gelatin approximates the density and viscosity of human muscle tissue and is used in certain tests of firearms and firearm ammunition. Approximating the density of human tissue may add to the realism by adding weight to the mannequin segments that approximates the weight of actual human components so that lifting a leg of the mannequin approximates the effort to lift a human leg. Alternatively, multiple staged reality modules may be present on single mannequin.

Filler pieces made of ballistic gelatin may have a finite life as that material degrades. An alternative material for filler pieces may be made from commercially available synthetic human tissue from a vendor such as SynDaver™ Labs that supplies synthetic human tissues and body parts. SynDaver™ Labs is located in Tampa, Fla., and has a web presence at http://www.syndaver.com. Some mannequin filler pieces may be sized to fill in around a specific staged reality module such as the spleen staged reality module. Others may be standard filler pieces for that particular mannequin. (A child mannequin or a mannequin for a super obese patient may have proportionately sized filler pieces).

Figure 4:
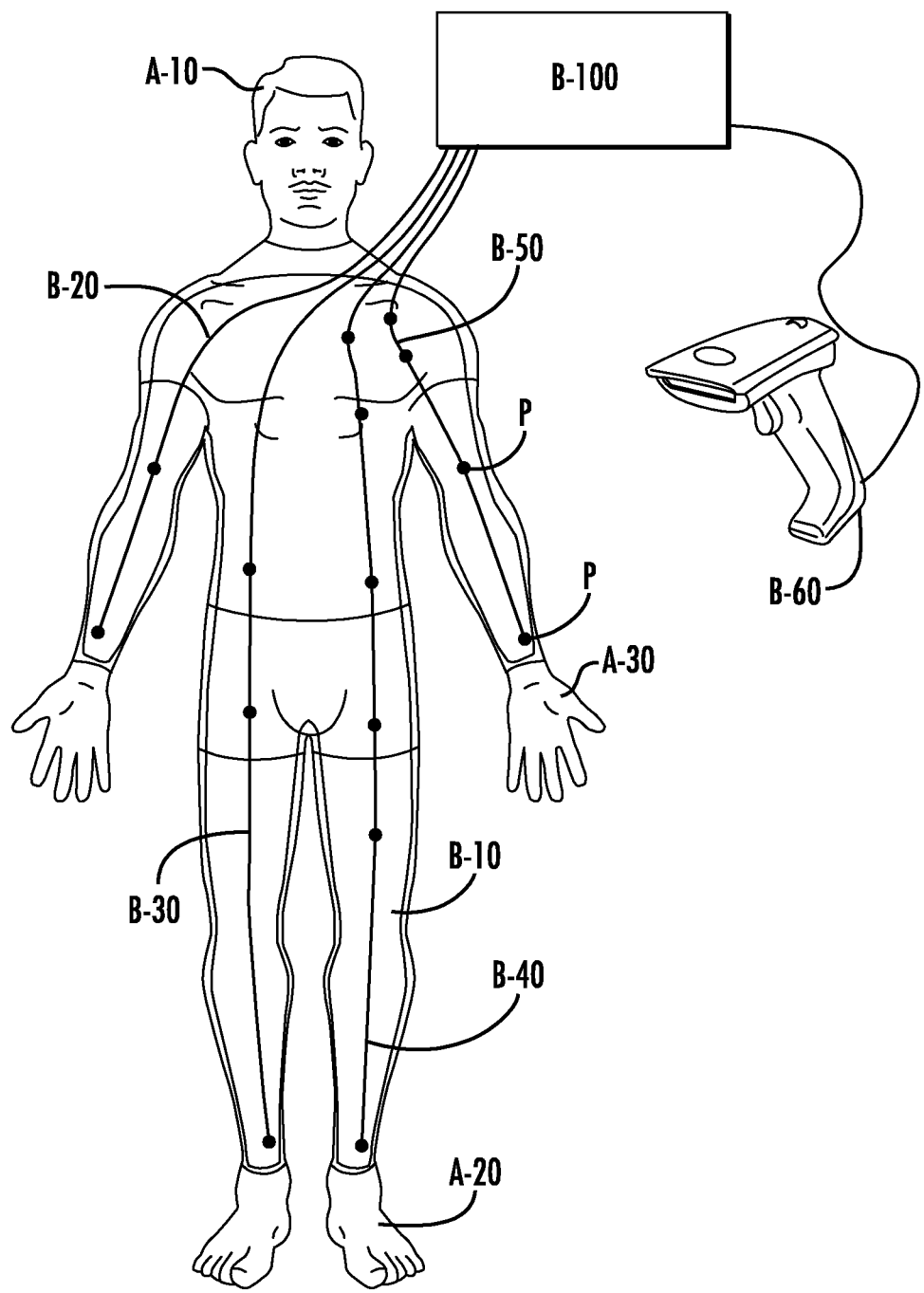
FIG. 4 shows a segmented mannequin A-100 with an open body cavity B-10 without the staged reality modules A-40 and A-50 that may be used in accordance with a non-limiting example.

FIG. 4 shows segmented mannequin A-100 with an open body cavity B-10 without the staged reality modules A-40 and A-50. FIG. 4 also lacks the mannequin filler pieces A-60 but retains the permanent mannequin parts A-10, A-20 and A-30.

The mannequin may include drain gutters and drain holes to remove excess liquid from the body cavity (not shown).

FIG. 4 includes a high level representation of the control system. Master-controller B-100 is connected to a series of umbilical cables, shown here in this example as umbilical cords B-20, B-30, B-40, and B-50. The mannequin may have fewer than four umbilical cables or more than four umbilical cables without departing from the teachings of the present disclosure. As described in more detail below, each umbilical cable may provide some combination of one or more pneumatic supply lines, one or more pressurized fluid supply lines, one or more instrument communication buses, and low voltage electrical supply to power module electronics and sensors.

FIG. 4 includes a series of ports P at various points along the four umbilical cables. The ports P allow for a staged reality module to be connected to an umbilical cord to receive pressurized fluids, pneumatic air (or other gas), connection to instrument communication buses, and low voltage electrical supply. While for simplicity, each port P is shown as an enlarged dot, a port is likely to have a series of different connections for different services provided to a module. Unless the port is located at the distal end of an umbilical cable, the port may appear as a short branch that is part of a T-connection to the umbilical cable.

A particular module may connect to one or many different connections. Several staged reality modules (such as A-40 and A-50) may be connected to ports along one umbilical cable (B-40). A designer of a comprehensive mediastinum module representing a number of structures found in the thorax cavity might find it useful to connect to ports on two parallel umbilical cables (such as B-30 and B-40) in order to minimize routing of connectors within the module.

FIG. 4 includes a bar code scanner B-60 that may be used to read bar code information from the packaging for the staged reality module. A bar code or other optical code could be used to convey a unique identifier for the module (source and unique serial number). A series of bar codes, a data matrix code (a two-dimensional matrix bar code), or some other optical code could be used on the module packaging to convey an array of data about the module. This data could be different for different types of modules but it may include the creation date of the module, the harvest date when the tissue components of the module were collected, and characterization data that may be relevant.

Characterization data may include:

A) a lot number which would provide a way to know that a given set of modules was created at the same time and intended to be used to provide substantially repeatable staged reality simulations;

B) a grade number which would apply across more than one lot so that modules created at different times but to a certain array of standards would have the grade number so that modules within the same grade number could be used if a sufficient number of modules within a particular lot number were not available;

C) an indication of the level of blockage of certain vessels;

D) an indication of the level of pliability/stiffness of certain tissue structures (which may increase the level of difficulty for certain procedures and mimic characteristics of certain patient populations);

E) an indication of the level of obesity associated with this module which may include the use of simulated fatty material that was added to the module to obfuscate the structure of the underlying tissue as often happens in actual surgery.

Inflation and Deflation of Lungs in an Organ Block

Where the organ block includes lungs, the lungs can be inflated and deflated using the methods described herein.

Inflation and deflation of lungs of a real patient causes the rise and fall of the mediastinum. To simulate this, an appropriate volume of air or some other fluid can be used to inflate and deflate an appropriately sized and placed container hidden under the tissue to be animated with movement. For example a respiration rate of 20 breaths per minute can be simulated by periodically expanding an air bladder such as a whoopee cushion, or an empty one-liter IV bag that is folded in half.

Rather than merely animating the tissue by causing it to rise and fall, one can connect lungs to a source of gas, such as air or nitrogen, and cycle the air going into and out of the lungs in such a way as to mimic respiration. For example, a bellows or an "Ambu bag," can be used to provide a "pulsatile" air supply. A suitable arrangement is described, for example, in U.S. Patent Publication No. 2013/0330700.

Figure 5:
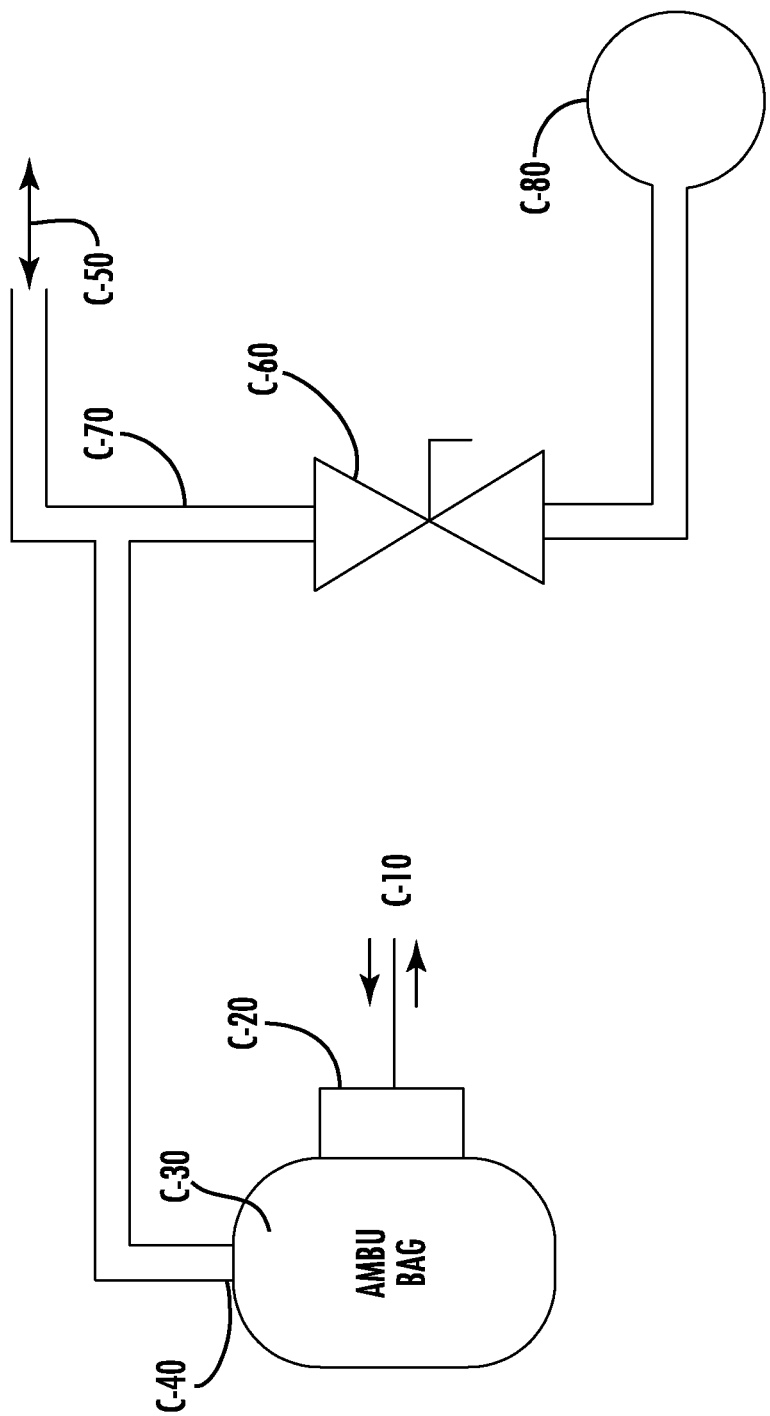
FIG. 5 shows a diagram for a pulsatile air pump that may be used in accordance with a non-limiting example.

In one embodiment, the lungs on a simulated patient can be inflated and deflated using the pulsatile air pump shown in FIG. 5. The air provided to the pulsatile air supply on the umbilical cable can be generated as symbolized by elements in FIG. 5. A linear input source (potentially stabilized by a linear bearing) moves a contact element C-20 relative to an anchored Ambu bag C-30. An Ambu bag (also known as a bag valve mask ("BVM")) is a hand-held device used to provide positive pressure ventilation to a patient that is breathing inadequately or not at all. The Ambu bag has a number of one way valves useful for this purpose.

One of skill in the art will recognize that moving the contact element C-20 relative to the Ambu bag will mean that for a portion of the stroke of the linear actuator C-10 that the contact element does not impact the Ambu bag. Thus the input to the Ambu bag C-30 can be altered from a sinusoidal input to more of a pulsatile input. Adjustments to the size of the Ambu Bag or its analogous replacement, the size of the contact element C-20 and the stroke length of the linear actuator after contact with the Ambu Bag will alter the air output at C-40. While the linear actuator C-10 could be a stepper-motor, other simpler solutions such as a windshield wiper motor could be used.

If this air source is used to animate a heartbeat then it would need to operate at a reasonable pulse rate for example 78 beats per minute. This pulse rate could be adjustable if desired or relevant to the staged reality.

Alternatively, if the air source is used to animate movements in response to respiration, then the pulses per minute would need to be reasonable for a patient undergoing surgery.

Fine tuning to control the amount of air C-50 provided to the umbilical cable (not shown) or a series of two or more umbilical cables via a header (not shown), may be achieved by a ball valve C-60 connected via Tee joint C-70. The ball valve C-60 may be used to divert air to bladder C-80 (such as a pair of balloons one within the other). The bladder should be operated in an elastic range so that the expanded bladder presses the air back towards the Ambu Bag when the Ambu Bag is not being compressed by the contact element C-20. The bladder may be connected to the air line by a segmented air nipple.

It may be desirable to maintain the pulsatile air system as a closed system so that one or more animation bladders connected to the ports of the one or more umbilical cables operate to force back the air into the tubing through operation of the bladder in an elastic range and the weight of the animated tissue.

Figure 6:
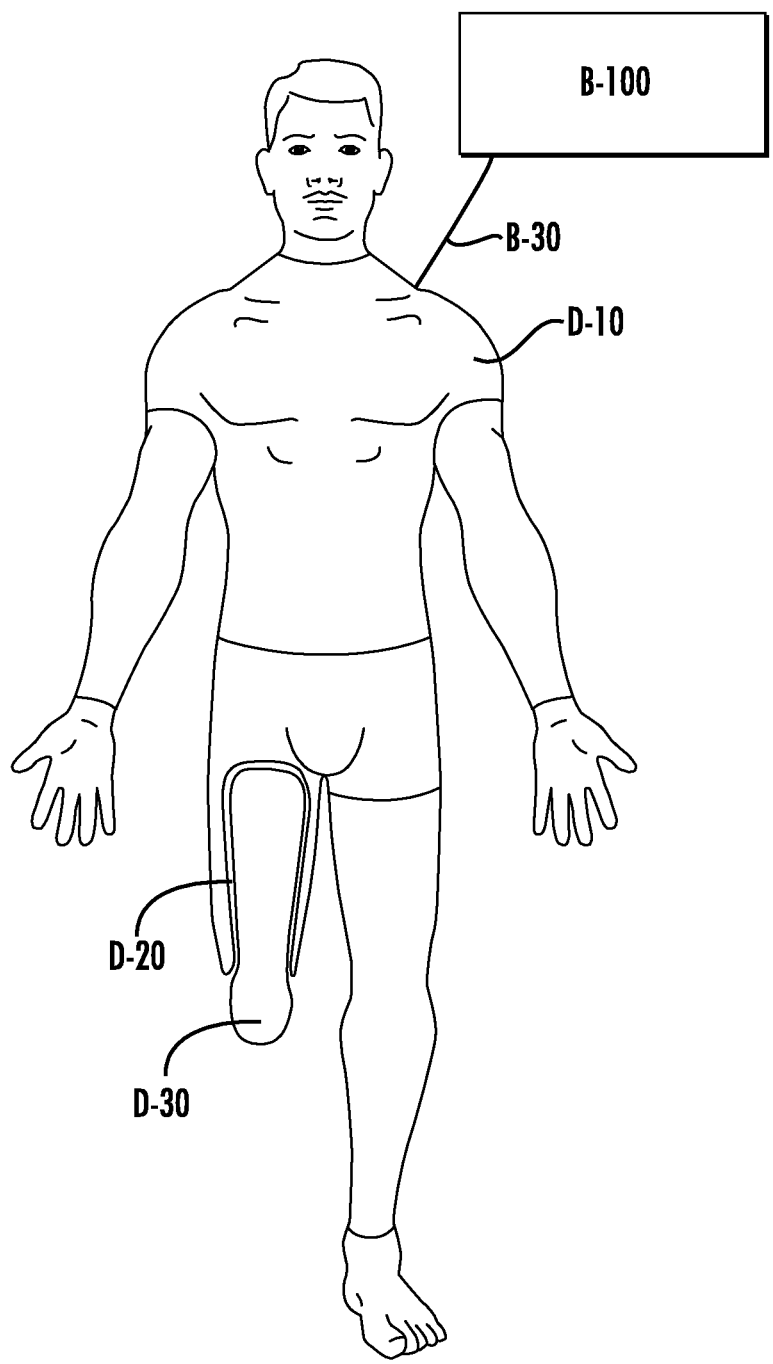
FIG. 6 shows a leg trauma mannequin D-10 that may be used in accordance with a non-limiting example.

FIG. 6 shows a leg trauma mannequin D-10 that includes the master controller B-100 and shows the shoulder portion D-10 and the leg area D-20 with an animated tissue portion D-30. The portion of the leg shown by D-20 and D-30 could be included as part of the animated tissue cassette.

In another embodiment, a more sophisticated system can be used to inflate and deflate the lungs, if desired. For example, a lung inflation/deflation system can include the following parts/sub-systems:

a. Programmable Logic Controller (PLC), such as an industrial computer that is designed to run 24/7 and to control machines, b. Human-Machine Interface (HMI), such as a touchscreen used to run/control the machine, c. Database of waveforms, where the waveforms reside in a non-volatile memory board or card and are accessed by the PLC. For heart beats, these waveforms can look like EKG traces, and for lung functions, including coughs and sneezes, these wave forms can look like audio recordings of the sound made during a cough or sneeze, d. Servo-Controller Power Amplifier, similar to a highfidelity analog sound amplifier such as those found in a stereo systems, e. Servo Motor, where the term "servo" indicates that there is a feedback loop between the signal fed to the amplifier and the actual motion of the servo motor. The motor is an electric motor, which is connected to, and draws power from, the amplifier. In this manner, when the amplifier outputs a waveform, the motor connected to it will dutifully follow the exact waveform it is being tasked to reproduce, f. Actuator, where the servo motor drives a lead screw in order to convert rotational motion to linear motion. The actuator is attached to bellows.

g. Bellows, which form an expandable chamber (for example, a rubberized and expandable chamber) that pushes air out and draws air back in again, all in direct proportion to the linear motion of the lead screw, h. Air output, where air coming out of the bellows passes through an air hose connection that connects, directly or indirectly to one or more balloons attached to or present in a heart, or directly to the windpipe or bronchus of the lung(s), i. Air make-up valve, which valve opens when needed to begin a cycle. The opening and closing of the valve can be controlled by the PLC, j. An optional isolation valve, which functions as a liquid trap, and which can optionally include a filter, such as a HEPA filter. The isolation valve serves to prevent liquids from the animal heart, lung, or other biological components of the organ block from coming into the expensive bellows and decomposing. This valve can also be connected to the PLC, and, in one embodiment, can include a detector to determine whether liquids are present, and, optionally, can shut the system down if a pre-determined volume of liquid is detected.

k. Pressure transducer, which is an accurate pressure gauge, ideally connected to the PLC, used to size the heart or lungs (and thus prevent over-filling), and to scale the waveforms, l. Connection to the organs, such as "quick-connect" fittings which allow hoses to go from the pump system to the "driven" organ.

The "bellows" element can alternatively be a bladder, such as an automotive ride-leveler industrial bladder.

Simulated Heartbeat

In one embodiment, the invention relates to an animal or human heart, in which from one to four balloons are placed within from one and four ventricles (typically with only one balloon per ventricle). The inflation and contraction of the balloon replicates a heartbeat.

Anywhere from one to four balloons can used, in anywhere from one to four ventricles, depending on the type of surgery to be simulated. The balloons are inflated with air, and allowed to deflate. The inflation and deflation of the balloons causes real or fake blood to circulate through the simulated "patient," or at least those parts of which that are exposed to the surgeon undergoing training.

By placing the balloon(s) inside of the ventricles, one can reasonably accurately reproduce the movement of the heart. That is, the heart is a muscle that expands and contracts. The inflation of the balloon causes active expansion, and the deflation of the balloon causes only passive contraction.

The addition and removal of a gas to the balloon can be controlled using the same mechanisms described above for moving a gas into and out of the lungs, except that the gas is moved in and out of a balloon, placed inside the heart, rather than the lungs.

Figure 7:
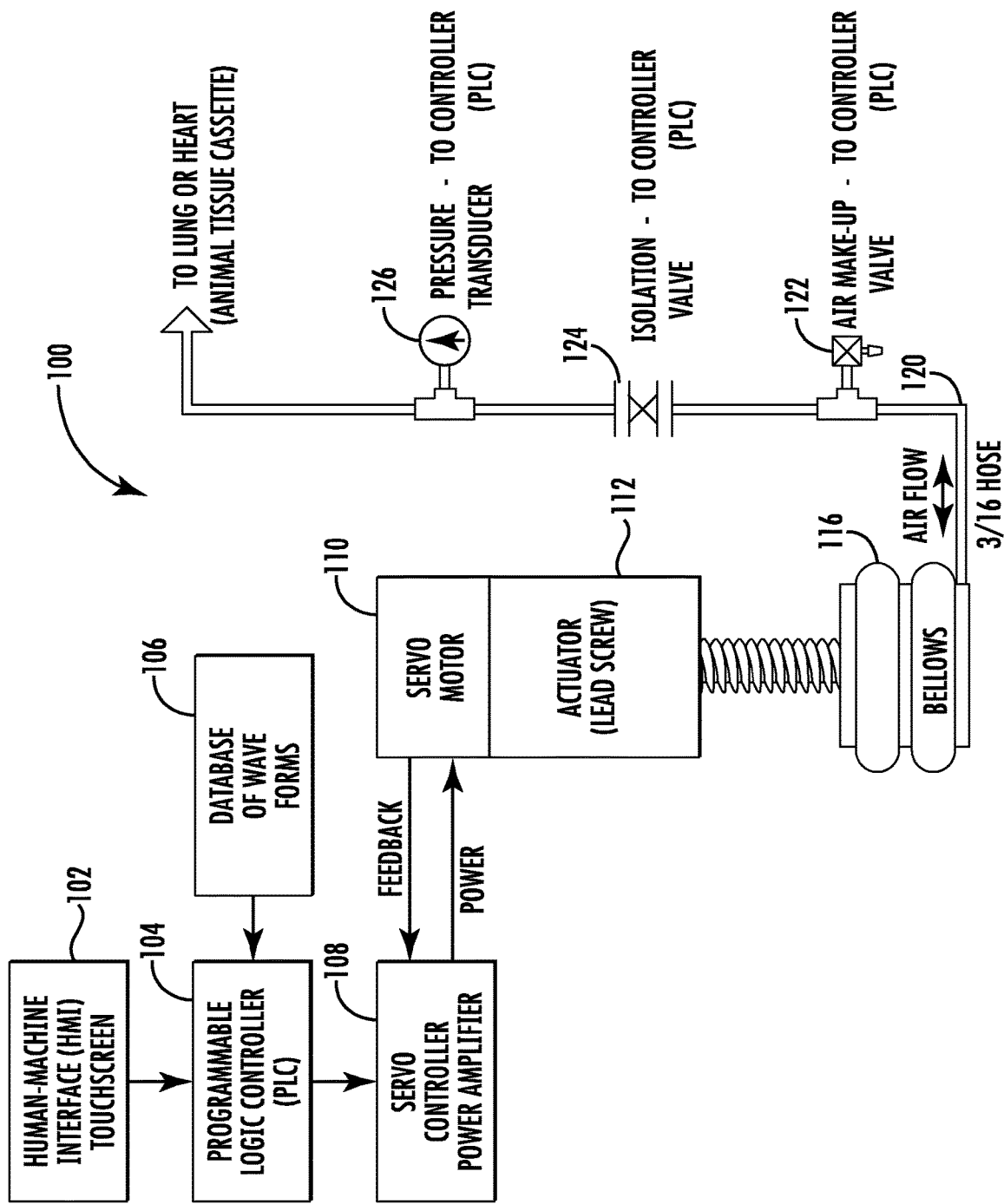
FIG. 7 is a block diagram of a system that can be used for inflating the lungs and/or heart in accordance with a non-limiting example.

A system 100 for inflating the lungs or the heart is shown in FIG. 7. A human-machine interface (HMI) 102 equipped with a touchscreen is connected to a programmable logic controller (PLC) 104, which includes or is attached to a database 106 of suitable waveforms. The waveforms can be used to simulate different types of breathing or different types of heartbeats. For example, a waveform can be used to simulate a normal heartbeat, cardiac arrest, various arrhythmias, and a flat-line (i.e., no pulse). Similarly, a waveform can be used to simulate normal breathing, shallow breathing, coughing, sneezing, sleep apnea, choking, and the like.

The PLC 104 is attached to a servo controller 108, which includes a power amplifier. The servo controller sends power to a servo motor 110, which sends feedback to the servo controller. The servo motor 110 is connected to an actuator 12, which actuator includes a means for translating energy into linear motion.

This can be, for example, a lead screw, ball screw, or rocker screw. Linear motion, or motion that occurs along a straight line, is the most basic type of movement. There are a number of linear energy devices enabling work functions like pumping. Electro mechanical actuators, which utilize an electric motor, can be used for these tasks. The motor turns a screw, such as a lead screw, ball screw, or rocker screw. Machine screw actuators convert rotary motion into linear motion, and the linear motion moves bellows up and down.

Bellows 116 are present in an actuator assembly to transfer pressure into a linear motion, or linear motion into pressure, depending on whether a gas is being blown into the lungs or heart, or being removed from the lungs or heart.

Edge welded bellows allow a long stroke, excellent media compatibility, and high temperature and pressure capabilities. Edge welded bellows also provide extreme flexibility in the design to fit size, weight, and movement requirements and allow the movement to be driven by internal or external forces. Bellows actuators can be used in valve applications, where pressure is internal or external to the bellows. Custom flanges, end pieces and hardware can be integrated into the assembly as appropriate.

The bellows is attached to an appropriately-sized hose 120, typically between ¼ and 1 inch in diameter, more typically ⅜ or ½ inch in diameter, which allows for the passage of a gas. The tubing can pass through an air make-up valve 122, an isolation valve 124, and a pressure transducer 126, any and all of which can be connected to the PLC. Once the appropriate pressure is attained, the gas can pass to the lung(s) and/or heart. The screw can be moved in one direction to fill the heart/lungs, and in the other direction to withdraw gas from the heart/lungs.

Master-Controller

The surgical simulator can be controlled using a master-controller. Master-controller B-100 is shown in FIG. 4 as a single component but it may in practice be distributed over several pieces of equipment.

Master-controller provides to the umbilical cables one or more pneumatic supplies. One pneumatic supply may be a closed loop system where air flow passes into and back from the umbilical cables on a periodic basis. For example, to support a staged reality of a beating heart, one pneumatic supply line may have air that pulses into the pneumatic line at 78 beats per minute. Optionally, this rate may be adjustable and may be altered to simulate a heart that stops or goes into some form of distress. Inflatable elements within the staged reality modules may thus expand and contract as paced by the pulses of air. Having a closed system avoids situations where staged reality module elements are overfilled. The amount of air provided by the pulse into the pneumatic line may be fine-tuned by the operator in order to adjust the simulation.

A pulsatile pump which better emulates a heartbeat than a sinusoidal oscillation of air in the pneumatic line may be included in the master-controller or the master-controller may receive pulsatile air from an external pulsatile pump. One suitable pulsatile pump is described in U.S. Pat. No. 7,798,815 to Ramphal et al. for a Computer-Controlled Tissue-Based Simulator for Training in Cardiac Surgical Techniques (incorporated herein by reference). A pulsatile pump may be created as indicated in FIG. 5.

Additional pneumatic supply lines at various target air pressures may be included in the umbilical cable.

The umbilical cable may include lines at ambient pressure (vented to ambient) or at a slight vacuum to allow expanded balloon-type structures to be emptied.

The master-controller B-100 (FIG. 4) may provide one or more fluids. The fluids may contain medical grade ethanol, dyes, and thickening agents. Medical grade ethanol has been found useful in maintaining the staged reality modules and in making the staged reality modules inhospitable to undesired organisms. Ethanol is useful compared to other chemicals which may be used to preserve tissue in that the ethanol maintains the pliability of the tissue so that it behaves like live tissue in a patient. A mixture with 40% ethanol works well, but the mixture should be made with an effort to avoid flammability when exposed to sparks or a cauterization process. Ethanol is desirable in that it does not produce a discernable odor to remind the participant that this is preserved tissue.

The storage life of some staged reality modules may be extended by storing them with fluid containing ethanol. A particular staged reality module that is not expected to be exposed to ignition sources should be made with an ethanol mixture that would be safe to have in proximity in a mannequin adjacent another staged reality module that did have ignition sources.

The master-controller may isolate the umbilical cable or cables from the fluid supply to allow the replacement of a module to allow the trainee to repeat a simulation with a new staged reality module.

Some staged reality modules may have prepared the module by connecting the venous and arterial systems together so that one pressurized fluid supply may animate both the arterial and venous vessels by filling them with colored fluid. The pressure for the fluid may be maintained by mere fluid head as an IV bag is suspended at a desired height above the master-controller or the master-controller may provide fluid at a given pressure using conventional components.

The umbilical cable may be provided with two blood simulating fluids, one being dyed to resemble arterial blood and a second dyed to resemble venous blood.

When the mannequin is to be used outdoors with a low ambient temperature, the staged reality module may have a circulation path that allows a warm fluid (approximately body temperature) to be circulated through the staged reality module and the umbilical cable to maintain the warmth of the tissue in the staged reality module. For staged reality modules that are expected to be completed within a short period of time, the staged reality module may be preheated to body temperature before the staged reality event and the fluids provided may be warmed to avoid cooling the staged reality module even when the fluid merely fills vessels in the staged reality module and is not circulated.

The umbilical cable may be provided with fluid lines for one or more non-blood fluids to be simulated such as digestive fluids, cerebral-spinal fluids, lymphatic fluids, fluids associated with pulmonary edema, pleural effusions, saliva, urine, or others fluids depending on the disease or trauma to be simulated.

The fluid and pneumatic connections used to connect the staged reality module to the various supplies on the umbilical cable may be any suitable connector for the desired pressure. Quick-connect fittings may be preferred so that the act of replacing a module with a similar module to allow the trainee to try it again may be accomplished quickly.

Depending on the quick-connect fitting used, the port may need to have blanks inserted to close the port to flow. When a module is to be connected to the port, the blank is removed and the module is connected.

The master-controller (B-100) may record the volume of fluids and gas provided to the particular lines or alternatively the pressure maintained on particular lines over time. This data record may be used to assess when a trainee effectively ligated a blood vessel or shut off some other structure such as a urinary tract.

The umbilical cable may include one or more instrument control cables. Control cables with common interface standards such as USB (Universal Serial Bus) may be used. The USB connection may be used to provide power to instruments and local logic devices in the staged reality modules. One of skill in the art will recognize that other data communication protocols may be used including RS-232 serial connection, IEEE 1394 (sometimes called Fire Wire or i.LTNK), and even fiber optic cable connections.

The USB connection allows for communication between a module and the master-controller. Depending on the staged reality presentation the communication may be to the module such as:

A) The master-controller (B-100) may send random or triggered commands for a staged reality component to twitch within a staged reality module.

B) The master-controller (B-100) may send a command to one or more staged reality modules to instigate quivering such as may be seen from a patient in shock. The staged reality module may implement quivering by opening and closing a series of small valves to alternatively connect a small balloon like structure to a high pressure gas via a port on the umbilical cable or to a vent line in the umbilical cable via the umbilical cable port. The valves providing the pressurized gas or venting of the balloon-like structure may be under the local control of logic within the staged reality module or they may be controlled directly from the master-controller.

C) The experience of staged reality may be increased by having more than one staged reality module quiver at the same time. Mannequins may make gross motions in response to pain such as sitting up or recoiling to add to the staged reality. This may startle the participant, but that may be a useful addition to the training.

The USB connection allows for communication from the staged reality module to the master-controller such as a time-stamp when the module detects the surgeon starting to cut into a portion of the module, pressure readings, accelerometer indications (respect for tissue).

The master-controller (B-100) may receive input from a simulation operator. The simulation operator may trigger adverse events that complicate the staged reality scenario such as a simulated cardiac event. The adverse event may be added to challenge a participant that has already demonstrated mastery.

The master-controller (B-100) may serve as part of a data collection system that collects data about the training of each particular participant so that the effectiveness of one training regime for one population of participants can be compared with the effectiveness of another training regime on another population of participants so that the differences of effectiveness can be quantified.

The master-controller (B-100) may have access to the training records for a particular participant in order to assess the need for additional repetitions of a particular training module.

Use of Bar Code Scanners

A bar code scanner B-60 can also be used to read bar codes on equipment or faux drug delivery devices to augment the simulation with recording the receipt of the therapy from the equipment or provision of a specific amount of a specific drug (even if no drug is actually delivered to the mannequin). This information may be used by the master-controller or communicated to one or more staged reality modules to alter the staged reality. For example, the intramuscular or intravenous delivery of a drug may alter the rate of bleeding, the heart rate, or some other parameter that impacts the presentation of the staged reality.

Representative Endoscopic Surgical Simulator

Endoscopic procedures can be simulated, for example, using the Endoscopy VR Simulator from CAE Healthcare. This simulator is a virtual reality endoscopic simulation platform that uses realistic, procedure-based content to teach cognitive and motor skills training. It is an interactive system with tactile feedback that permits learning and practice without putting patients at risk. The tissue, while not animal tissue, looks real, and 'moves' when it is touched. The virtual patient exhibits involuntary muscle contractions, bleeding, vital sign changes, etc., and the surgeon feels feedback resistance during the simulated procedure.

III. Robotic Surgical Instruments

In the systems described herein, one or more surgeons performs surgery on the animal tissue, organs, and/or organ blocks using robotic surgical instruments.

Typically, the robotic surgical devices include one or more arms, which control one or more tools, such as an endoscope (which provides the surgeon with the ability to see inside of the patient, and, typically, a tool selected from the group consisting of jaws, scissors, graspers, needle holders, micro-dissectors, staple appliers, tackers, suction irrigation tools, clip appliers, cutting blades, cautery probes, irrigators, catheters, suction orifices, lasers, and lights.

In robotically-assisted telesurgery, the surgeon typically operates a master controller to control the motion of surgical instruments at the surgical site from a location that may be remote from the surgical simulator (e.g., across the operating room, in a different room, or a completely different building from the surgical simulator).

The master controller B-100 usually includes one or more hand input devices, such as hand-held wrist gimbals, joysticks, exoskeletal gloves or the like. These control the movement of one or more of the robotic arms. Occasionally, line-of-sign/gaze tracking and oral commands are used to control movement of one or more of the robotic arms, and/or the audio/video components that transmit signal back to the surgeon.

Gaze tracking is described, for example, in U.S. Patent Publication No. 2014/0282196 by Zhao et al. A gaze tracker can be provided for tracking a user's gaze on a viewer. Preferably, the gaze tracker is a stereo gaze tracking system. An example of such a gaze tracking system is describe in U.S. Patent Application Ser. No. 61/554,741 entitled "Method and System for Stereo Gaze Tracking." If the viewer only has a single two-dimensional display screen, however, any conventional gaze tracker may be usable with a video-based system preferred since it is non-contacting.

When the surgeon is in the same room as the robotic surgical device, these devices can be operatively coupled to the surgical instruments that are releasably coupled to a surgical manipulator near the surgical simulator ("the slave"). However, when the surgeon is remote from the actual room in which the surgery is taking place, these devices are coupled using the internet, or an intranet, preferably using some form of cloud computing.

In this case, the master controller B-100 controls the instrument's position, orientation, and articulation at the surgical site. The slave is an electro-mechanical assembly which includes one or more arms, joints, linkages, servo motors, etc. that are connected together to support and control the surgical instruments. In a surgical procedure, the surgical instruments (including an endoscope) may be introduced directly into an open surgical site, through an orifice, or through cannulas into a body cavity present in the animal tissue, organs and/or organ blocks.

For minimally invasive surgical procedures, the surgical instruments, controlled by the surgical manipulator, can be introduced into a simulated body cavity through a single surgical incision site, multiple closely spaced incision sites on the simulated body, and/or one or more natural orifices in the anatomy of the organ and/or organ block (such as through the rectum where a porcine or other animal gastrointestinal system is used as the organ block).

For some minimally invasive surgical procedures performed through particularly small entry ports, multiple surgical instruments may be introduced in a closely gathered cluster with nearly parallel instrument shafts.

In one embodiment, the surgical systems and techniques maintain a common center of motion, known as a "remote center," at an area near the anatomical entry point. However, where there is a particularly narrow surgical incision or a particularly narrow natural orifice, such as an animal throat or cervix, this may result in the collision of the proximal ends of the surgical instruments. To control the surgical instruments while minimizing the occurrence of surgical instrument collisions, it may be desirable to use a robotic system such as that described in U.S. Patent Publication No. 2014/0236175 by Intuitive Surgical Operations, Inc.

A more detailed explanation of certain the components of robotic systems is provided below:

A robotic surgical system includes a master system, also referred to as a master or surgeon's console, for inputting a surgical procedure and a slave system, also referred to as a patient-side manipulator (PSM), for robotically moving surgical instruments at a surgical site within a patient. The robotic surgical system is used to perform minimally invasive robotic surgery. One example of a robotic surgical system architecture that can be used to implement the systems and techniques described in this disclosure is a da Vinci®. Surgical System manufactured by Intuitive Surgical, Inc. of Sunnyvale, Calif. Alternatively, a smaller scale robotic surgical system with a single manipulator arm may be suitable for some procedures. The robotic surgical system also includes an image capture system, which includes an image capture device, such as an endoscope, and related image processing hardware and software. The robotic surgical system also includes a control system that is operatively linked to sensors, motors, actuators, and other components of the master system and the slave system and to the image capture system.

The system is used by a system operator, generally a surgeon, who performs a minimally invasive simulated surgical procedure on a simulated patient. The system operator sees images, captured by the image capture system, presented for viewing at the master system. In response to the surgeon's input commands, the control system effects servo-mechanical movement of surgical instruments coupled to the robotic slave system.

The control system includes at least one processor and typically a plurality of processors for effecting control between the master system, the slave system, and the image capture system. The control system also includes software programming instructions to implement some or all of the methods described herein. The control system can include a number of data processing circuits (e.g., on the master system and/or on the slave system), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system may support wireless communication protocols such as Bluetooth, IrDA, HomeRF, IEEE 802.11, DECT, and Wireless Telemetry.

The robotic surgical system can also include an instrument chassis that couples to the slave system. The instrument chassis provides a common platform for coupling surgical instruments and endoscope for introduction into an entry point on the simulated patient. In one embodiment, the entry point can be a mouth, where access to the throat or larynx is desired, the rectum where access to the gastrointestinal system, or, more particularly, to the colon, is desired, or previously-prepared or surgically created openings or orifices.

In one embodiment, the system can also include an instrument chassis having a proximal section and a distal section. The chassis supports an endoscope. Generally, the dimensions and shape of the chassis at its distal section are typically reduced compared to its proximal end, to minimize the volume of the surgical equipment near the surgical entry point. Instrument interfaces can be movably mounted to the proximal section of the instrument chassis. Surgical instruments can be mounted at the proximal end to the instrument interface. Surgical instruments can be mounted at its proximal end to the instrument interface. The interface drives movable components in the surgical instrument as described in U.S. Pat. No. 6,491,701 which is incorporated by reference herein in its entirety. The interface drives the instrument in a similar way. The surgical instruments are also movably coupled to the distal section of the chassis. The instrument interfaces are mounted to the proximal section of the chassis such that rotational and linear motion is permitted. Specifically, an instrument interface mounting or a flexible instrument shaft permits a pitch motion of the instrument interfaces relative to the chassis, a yaw motion of the instrument interfaces relative to the chassis and an insertion sliding motion of the instrument interfaces relative to the chassis. The system can function in a manner similar to the manner in which chopsticks operate, in that small motions at the proximal end of the tool, near a pivot location, can correspond to larger motions at the distal end of the tool for manipulating objects.

An actuation system operates the components of instrument, such as an end effector and various wrist joints. An actuation system operates the components of instrument, such as an end effector and various wrist joints. The actuation systems can include motors, actuators, drive systems, control systems, and other components for effecting controlling the instruments. An interface actuation system controls the movement of the instrument with respect to the chassis, and an interface actuation system controls the movement of the instrument with respect to the chassis. The surgical system can be configured to manipulate one, two, or more instruments.

Some robotic surgery systems use a surgical instrument coupled to a robotic manipulator arm and to an insertion linkage system that constrained motion of the surgical instrument about a remote center of motion aligned along the shaft of the surgical instrument and coincident with a patient entry point, such as an entry incision. Further details of these methods and systems are described in U.S. Pat. Nos. 5,817,084 and 6,441,577, which are incorporated by reference herein in their entirety.

Actuators can be operably coupled to interface discs. A more detailed description of the interface discs and their function in driving a predetermined motion in an attached surgical instrument is fully described, for example, in U.S. Pat. No. 7,963,913, filed Dec. 10, 2006, disclosing "Instrument Interface of Robotic Surgical System," which is incorporated by reference herein in its entirety.

Various embodiments of surgical instruments, end effectors, and wrist mechanisms are explained in detail in U.S. Pat. Nos. 5,792,135; 6,331,181; and 6,817,974, which are incorporated by reference herein in their entirety.

Software Control

One or more elements in embodiments described herein can be implemented in software to execute on a processor of a computer system such as control system. When implemented in software, the elements of the embodiments described herein are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

The processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

Surgeon's Remote Control of Instruments

As discussed above, in use, the surgeon must control a number of surgical instruments. This can be performed using, for example, gimbals, foot pedals, oral commands, and/or "gaze tracking," although gaze-tracking is not a popular method of controlling surgical instruments at the present time. Motions by the surgeon are interpreted by software, and a signal can be transmitted, either through a wire, or wirelessly, to a controller connected to the robotic instrument, which translates the signal into instructions for moving one or more robotic arms.

As the signal is received, and the robotic arms are moved, it is critically important that the surgeon can see how the instruments are moved, and how the instruments in turn affect the "patient." That is, if there is bleeding, changes in heartbeat or respiration, and the like, the physician must respond in a timely manner. Accordingly, a "live" video, and, optionally, audio feed is transmitted back to the surgeon.

It is critically important to minimize latency in the signal being passed back and forth between the surgeon and the robotic system. Ways to control latency are discussed in more detail below.

U.S. Pat. No. 6,659,939 entitled "Cooperative Minimally Invasive Telesurgical System," which is incorporated herein by reference, provides additional details on a medical robotic system such as described herein.

Typically, a robotic system includes an image capture device, which is preferably a high-definition digital stereo camera that generates a video stream of stereo images captured at a frame rate of the camera, such as thirty frames per second. Each frame of stereo images includes a left stereo image and a right stereo image. In use, the image capture device captures video and, optionally, audio feed at the surgical site, providing one or more surgeons with real-time information on how the operation is proceeding.

The system uses a processor, programmed to process images received from the image capture device and display the processed images on a viewer. The viewer is preferably a stereo viewer having left and right display screens for respectively displaying left and right stereo images derived from the left and right stereo images captured by the image capture device.

A variety of input devices are provided to allow the surgeon(s) to control the robotic system. For example, user interfaces can include wrist gimbals, foot pedals, microphones, speakers, and gaze trackers. These input devices (also referred to as "masters") can also include any conventional computer input device, such as a joystick, computer mouse, keyboard, microphone, or digital pen and pad. Each of these devices can optionally be equipped with an on-off switch. The microphone facilitates user input to a voice recognition function performed by the processor, and the speaker can provide auditory warnings or action prompts to the user.

A gaze tracker can include eye tracking hardware in the viewer that communicates information related to such eye tracking to the processor. The processor processes the information to determine a gaze point of the user on a display screen of the viewer. In one example, the viewer may include one or more light sources, such as one or more infrared Light Emitting Diodes (IR LEDs) for directing light onto an eye of the user, a reflected light or image capturing device such as a Charge Coupled Device (CCD) camera, and one or more mirrors such as Dichroic mirrors for directing the reflected light from and/or image of the eye of the user to the reflected light or image capturing device. Information related to the reflected light or captured image can then be transmitted from the reflected light or image capturing device to the processor, which analyzes the information using known techniques to determine the gaze and gaze point of the user's eye on the viewer.

Tools are provided so that they may interact with objects at a surgical site. The tools and the image capture device are robotically manipulated by the robotic arms to which they are attached (also referred to as "slaves"). The tools are controlled by movement of the robotic arms, which in turn is controlled by the processor, which in turn receives signals from the surgeon(s) via signals sent by the input device(s).

The system can include one, two, or more input devices, and tools. The number of input devices and tools depends one what is needed at the time for performing the desired robotic surgery.

The processor performs various functions in the robotic system, including controlling the movement of the robotic arms (and, hence, the robotic operation of the tools), as well as the image capture device in response to the surgeon's interaction with the input devices. The processor can also process images captured by the image capture device and send an appropriate signal for display on the viewer.

Although described as a processor, it is to be appreciated that the processor can be implemented by any combination of hardware, software, and firmware. Also, its functions as described herein may be performed by one unit or divided up among different components, each of which may be implemented in turn by any combination of hardware, software, and firmware. In performing its various tasks, the processor executes program code which is non-transitorily stored in memory.

The processor can also be used to perform a calibration function, where movements of one or more surgeons are calibrated based on user preferences.

If the user's gaze point is on an image of a robotically manipulated tool at the work site, then identification of the tool can readily be performed by, for example, using conventional tool tracking techniques and a previously determined transform which maps points in each tool's reference frame to a viewer reference frame. Additional details for tool tracking may be found, for example, in U.S. Patent Publication No. 2006/0258938 entitled "Methods and System for Performing 3-D Tool Tracking by Fusion of Sensor and/or Camera Derived Data During Minimally Invasive Robotic Surgery," which is incorporated herein by reference. Additional details for reference frame transforms may be found, for example, in U.S. Patent Publication No. 2012/0290134 entitled "Estimation of a Position and Orientation of a Frame Used in Controlling Movement of a Tool," which is incorporated herein by reference.

In addition to or in place of gaze tracking, the surgeon can identify the object to be viewed and/or controlled using any of the user input mechanisms provided, such as a Graphical User Interface (GUI) or a Voice Recognition System.

Once the object is identified, the object is highlighted in some fashion on the viewer. The processor can provide a signal to the surgeon, allowing the surgeon to confirm that the object that is highlighted is the correct object, using any appropriate input device. If the incorrect object is identified, the surgeon can adjust to this by recalibrating the instrument.

Some common ways to control multiple tools include having a surgeon select an action command, such as "IDENTIFY TOOL," which displays information on the tool on or adjacent an image of the tool on the viewer, and a command of "IDENTIFY MASTER," which identifies the master currently associated with the tool. The associated master in this case is the input device which controls robotic movement of the selected tool.

Another useful command is "STATUS," which provides status information for the tool being displayed on or adjacent an image of the tool on the viewer. The status information may include the remaining life of the tool in terms of hours, number of usages, or other maintenance and/or replacement measures. It may also include warnings if the usage reaches certain thresholds or certain conditions are met.

Another useful command is "SWAP TOOL," which allows the surgeon to control a different tool. One way to allow a surgeon to swap tools is to have a selectable icon displayed on the display screen of the viewer. The surgeon can select the selectable icon using an appropriate input device, such as a conventional computer mouse. Alternatively, the surgeon can use a command "SWAP MASTER," allowing the surgeon to select the icon of another master. This can disassociate the currently associated master from the tool and the master corresponding to the selected one of the selectable icons would be associated to the tool. The icon of the newly associated master would then be highlighted and user interaction with the newly associated master would now control movement of the tool.

Yet another useful command is "FOLLOW," which allows the image capture device to automatically move so that the working end of the selected tool remains in approximately the center of its Field of View (FOV). Additional details on such a coupled control mode may be found, for example, in U.S. Patent Publication No. 2010/0274087 entitled "Medical Robotic System with Coupled Control Modes," which is incorporated herein by reference.

Additional commands can be used to control movement of the tool, the arm, and/or the image capture device, for example, commands made to correct direction, such as "UP", "DOWN", "RIGHT", "LEFT", "FORWARD", and "BACK" in three-dimensional space. The correctional action may be a correctional sizing, such as "INCREASE WIDTH", "DECREASE WIDTH", "INCREASE LENGTH", "DECREASE LENGTH", "INCREASE DEPTH", and "DECREASE DEPTH" for a three-dimensional box.

Additional commands can be used to control the image capture device. For example, "ADJUST FOCUS," "ZOOM-IN" or "ZOOM-OUT" can be used for the well-understood purposes associated with these commands. Similarly, a command "ADJUST BRIGHTNESS" can be used to automatically adjust the brightness function on the image capture device, for example, as a function of a distance from the image capturing end of the image capture device to an object whose image is being viewed at the time inside the displayed box on the viewer. Commands of "INCREASE RESOLUTION" or "DECREASE RESOLUTION" can be used to adjust the resolution of the image captured by the image capture device.

Other commands that a surgeon may wish to use include "CONSTRAIN TOOLS," to establish a virtual constraint in which the processor, acting as a controller for robotically manipulating the tools, responds to such user selected action command by constraining commanded movement of the working ends of those tools to only move within an area/volume of the work site corresponding to the area/volume of the box defined on the viewer. Alternatively, such constraint may be to prohibit the tools from entering an area/volume of the work site corresponding to the area/volume of the box. As other examples, certain image characteristics in a region of interest defined by the box may be adjusted, images of objects within the box may be zoomed-in or zoomed-out, and the image within the box may be displayed on an auxiliary viewer that is being viewed at the time by an assistant.

These are merely examples of useful commands. Those of skill in the art will appreciate that there are a number of other suitable actions that can be defined and performed.

Additional language on robotic systems that can be used in the systems described herein can be found in U.S. Patent Publication No. 2014/0236175 by Intuitive Surgical Operations, Inc.

IV. Remote Control of Robotic Systems

Telesurgery can be used in order for a surgeon to perform surgery from a distance, or to provide consultation or education to another surgeon performing a real operation, where an expert surgeon may watch watching the real operation and instruct the doctor, where the surgery is performed on a surgical simulator. One or more of the surgeons can be located at a remote location, where a robot is used to carry out the surgery, using hand movements and other input from the surgeon at the remote location via a tele-robotic unit.

The robot can move the real endoscope or other surgical device according to the movements of the surgeon performed using the input devices described above.

A simulated procedure can be taught by one surgeon to another surgeon at a remote location in real-time using a video data feed. For example, a surgeon using a real endoscope looking at the surgical simulator, with real animal organs, which, depending on the organ, can beat like a beating heart or breathe like a living set of lungs, can move the endoscope inside the "orifices" of the simulated human patient, can receive video corresponding to data transmitted electronically to a remote point (e.g., from the Mayo Clinic or via the Internet), and an expert watching the operation in real-time can show the actual doctor performing the simulated surgery how to conduct the operation, or provide particular guidance to the other surgeon performing the operation. This guidance can be provided on a display screen in the actual operating room while the surgeon is operating on the simulated patient.

A storage library can be implemented, in which a library of simulations, problems encountered, etc. are stored for later retrieval by a student or surgeon. For example, an expert surgeon teaching surgery using the simulator can simulate a biopsy or how to use a laser or particular surgical device on a simulated patient with a particular abnormality or operation to be performed. This is particularly true where organs or organ blocks are selected which include the particular abnormality.

The present invention can thus be used in a telerobotics application for teaching surgery on a simulated surgical device, such as those described herein.

Force feedback may be provided to the surgeon by the instructor, where the instructor takes over control of the robotic instruments from the student.

A virtual surgery system according to an embodiment of the present invention can be used in which an input device is used by a user to perform virtual surgery as described above. The input devices can include one or more of a mouse device, a seven dimensional joystick device, a full size simulator, etc. The input device can also one or more of include a keyboard, a standard mouse, a three dimensional mouse, a standard joystick, a seven dimensional joystick, or a full size simulator with a full size mock-up of a medical or other industrial type instrument. Additionally, any of these input devices can be used in the present invention with force feedback being performed.

The signals, originating when the surgeon operates an input device, are transmitted through a wired or wireless connection, to a processor on the robotic surgical instrument, which is then translated to a command that moves the robotic arm, and the surgical tool attached to the arm.

The control of the telerobotic system is ideally handled in a manner which minimizes latency, so there is little perceived delay between the surgeon remotely directing the movement of the tool, the movement of the tool, and the video and, optionally, audio feed back to the surgeon.

One example of a suitable telerobotic communication system is described, for example, in U.S. Patent Publication No. 2013/0226343 by Baiden. Such a system can include a teleoperation center to transmit control data and receive non-control data by wireless connection to and from a surgeon, operating one or more input devices, and indirectly to and from the actual robotic system including the robotic arms and tools attached thereto.

The device used by the surgeon can include includes a transceiver for receiving and transmitting control and non-control data, respectively, and also a repeater for relaying control data to a robotic surgical system, and relaying non-control data back to the teleoperation center. The system can also include wireless repeaters to extend the communications distance between the site where the surgeon is controlling the robotic instruments, and the site where the instruments are located.

The electronics of the system can use control-specific input/output streams, and are, ideally, low latency. The electronics are preferably designed to be high speed and fast processing and to minimize latency. The system can include at least two main communication components: the first is a long distance directional transmitter/receiver, and the second is a transceiver.

A video system can perform image processing functions for, e.g., captured endoscopic imaging data of the surgical site and/or preoperative or real time image data from other imaging systems external to the simulated patient. The imaging system outputs processed image data (e.g., images of the surgical site, as well as relevant control and patient information) to the surgeon at the surgeon's console. In some aspects the processed image data is output to an optional external monitor visible to other operating room personnel or to one or more locations remote from the operating room (e.g., a surgeon at another location may monitor the video; live feed video may be used for training; etc.).

Remote surgery (also known as telesurgery) is the ability for a doctor to perform surgery on a patient even though they are not physically in the same location. Remote surgery combines elements of robotics, cutting edge communication technology such as high-speed data connections and elements of management information systems. While the field of robotic surgery is fairly well established, most of these robots are controlled by surgeons at the location of the surgery.

Remote surgery allows the physical distance between the surgeon and the simulated patient to be immaterial. It allows the expertise of specialized surgeons to be available to students worldwide, without the need for the surgeons to travel beyond their local hospital to meet the surgeon, or to a remote site where a simulated surgical center may be. A critical limiting factor is the speed, latency and reliability of the communication system between the surgeon and the robotic instrument where simulated patient is located.

Cloud Computing

Any communications approach which provides the desired low latency can be used, but cloud computing is preferred.

A cloud computing system is one where some part of the computing happens remotely through the internet (aka "the cloud"). In the case of robotic surgery conducted remotely, this will involve a surgeon inputting information regarding the movement of robotic equipment using essentially the same tools available to the surgeon when he or she is in the same room as the robotic surgical equipment (i.e., gimbals, controllers, foot pedals, line of sight devices, and voice commands), but sending the signals over the internet, so that the controls are translated into movement of the robotic arms at the remote site.

Simultaneously, or substantially so, video signals, showing the movement of the robotic arms, and providing a video feed of the surgery taking place, is transmitted back to the surgeon.

The data is, in effect, running on a server in a data center connected to the internet, perhaps thousands of miles away, rather than on a local computer.

In one embodiment, the cloud computing experience is perceptually indistinguishable from a local computing experience. That is, when the surgeon performs an action, the surgeon experiences the result of that action immediately, just as if the surgery was being performed in the same room as the robotic device, and can view the results on a video monitor.

In one embodiment, the cloud computing system is an "OnLive" system (now owned by Sony). The OnLive system for "interactive cloud computing" is one in which the "cloud computing" (i.e., computing on a server in the internet) is indistinguishable from what computing experience would be if the application were running entirely on a local computer. This is done by minimizing latency.

It is critically important to minimize latency, because robotic surgery requires perceptually instantaneous response times, which can otherwise be difficult to achieve, given the complexity, erratic motion and unpredictability of real-time visual imagery.

The vast majority of current services, applications and media available on the internet use existing infrastructure and its inherent limitations exceedingly well. These applications generally are those that are largely unidirectional and with loose response deadlines: they download software, content and media objects based on limited amount of user interaction. Other applications from the web download executable programs which are then run in a user's local machine environment, using the internet only for a limited exchange of data and commands. This methodology requires an end-user machine to have the full extent of computing power (e.g., processor, memory, storage and graphics) as well as entire programs to be downloaded into the local user environment. With an Interactive Cloud Computing ("ICC") system, expensive hardware, software, data, and complex processes can stay in the data center. This reduces the need, cost, complexity and energy consumption of end user computers. Further, by sharing the central systems among many users, any negative impacts associated with those systems are divided amongst the many users.

The cloud computing system not only has to provide adequate bandwidth to allow data regarding the movement of the robotic arms, and a live video feed of the operation as it is being conducted remotely, it also has to quickly process data (using interactive, cloud-based systems) and then provide (i.e., render) the resulting audio/video in the data center, compress the audio/video, and condition the compressed audio/video to be transmitted to the end user as quickly as possible, simultaneously as the user is providing real-time feedback (via gimbals, foot pedals, mice, line-of-sight, voice control, and/or other methods of controlling the movement of the robotic arms) based on those real-time-transmitted sounds and images.

The performance metrics involve bandwidth (i.e., data throughput). Generally, the more bandwidth, the better the experience. A 100 Mbps connection is much more desirable than a 5 Mbps connection because data downloads 20 times faster. For this reason, the systems described herein preferably have a bandwidth of at least 5 Mbps, more preferably, at least about 50 Mbps, and even more preferably, at least about 100 Mbps.

That said, with ICC, as long as the bandwidth required for the resolution of the video display, audio stream, and transmission of data relative to movement of the robotic arms has been met, there may not be much need for additional bandwidth. For example, if a user has a 1280×720p@60 frame/second (fps) HDTV display and stereo audio, a 5 Mbps connection will deliver good sound and video quality, even with highly interactive content, like the control of robotic arms for a remote surgical instrument. A 10 Mbps connection will fully support 1920×1080p@60 fps HDTV, a cell phone-resolution screen can be supported with 400 Kbps, and so on.

One significant aspect of the online-computing experience is that there be constant availability of data transfer. Commercial ISP connections often are rated in terms of availability (e.g., percentage of downtime, and sometimes with further statistical guarantees). For example, one can purchase a fixed downstream connection speed, for example, rated at 1.5 Mbps, using a T1 line or a fractional T1 line, or can use a cable modem connection that provides "up to" 18 Mbps downstream when a high-reliability application (e.g., an IP telephone PBX trunk line) is at stake. Although the cable modem connection is a vastly better value most of the time, because cable modem connections are typically not offered with availability guarantees, the business may not be able to risk the loss of its phone service if the cable modem connection "goes down" or if the bandwidth drops precipitously due to congestion.

While in other uses for data transfer, availability requirements may be less stringent, and users can tolerate Internet Service Provider ("ISP") connections that occasionally go down or are impaired (e.g., from congestion), this is not the case with telerobotics.

With telesurgery, availability is extremely important. The loss of a internet connectivity can be crippling when attempting to perform a simulated surgery, particularly where the "patient" can experience bleeding, and changes on breathing rate and heartbeat, simulating a failed surgical procedure, or an error that must quickly be corrected.

Performance metrics which are particularly relevant for telesurgery include:

1. Latency: the delay when packets transverse the network, measured using Round Trip Time (RTT). Packets can be held up in long queues, or delayed from taking a less direct route to avoid congestion. Packets can also be reordered between the transmission and reception point. Given the nature of most existing internet applications, latency is rarely noticed by users and then only when latency is extremely severe (seconds). Now, users will be noticing and complaining about latencies measured in milliseconds because of the accumulation of latency as messages route through the internet, and the immediate-response nature of interactive cloud computing.

2. Jitter: random variations in latency. Prior-technology internet applications used buffering (which increased latency) to absorb and obscure jitter. As a result, users have not noticed or cared about jitter, and the common preconception is that jitter is a technical detail that has no impact on user experience or the feasibility of provisioning internet applications. With interactive cloud computing, excessive jitter can have a significant impact on user experience and perceived performance, ultimately limiting the range of applications.

3. Packet Loss: data packets lost in transmission. In the past, almost all internet traffic was controlled by TCP (Transmission Control Protocol), which hides packet losses by asking for retransmissions without the user's knowledge. Small packet losses come with small increases in latency and reductions in bandwidth, essentially invisible to users. Large packet losses (several percent and up) felt like a "slow network" not a "broken network." With interactive cloud computing the additional round-trip latency delay incurred by requesting a resend of a lost packet potentially introduces a significant and noticeable lag.

4. Contention: multiple users competing for the same bandwidth on an ISP's network in excess of the network's capacity, without a fair and consistent means to share the available throughput. As applications and use of Internet infrastructure continue to grow, old assumptions about the rarity or improbability of contention are being overturned. Contention leads to exacerbation in all three areas: latency, jitter and packet loss, mentioned above.

It can be important to minimize all of these aspects.

When the surgeon performs an action on a surgical instrument connected to OnLive (e.g., moves an input device), that action is sent up through the internet to an OnLive data center and routed to a server that is controlling the robotic instrument the surgeon is using. The processor computes the movement of the robotic instrument being controlled by the input device, based on that action, then the signal is quickly compressed from the server, and the signal is translated by a processor into movement of a robotic tool. Similarly, video, and, optionally, audio feed is compressed, transmitted, decompressed, and displayed on the surgeon's video display. The signals can be decompressed using a controller (for example, a PC, Mac or OnLive MicroConsole™). The entire round trip, from the time the input device is manipulated to the time the display or TV is updated is so fast that, perceptually, it appears that the screen is updated instantly and that the surgery is actually being performed locally.

The key challenge in any cloud system is to minimize and mitigate the issue of perceived latency to the end user.

Latency Perception

Every interactive computer system that is used introduces a certain amount of latency (i.e., lag) from the point the surgeon performs an action and then sees the result of that action on the screen. Sometimes the lag is very noticeable, and sometimes it isn't noticeable. However, even when the brain perceives response to be "instantaneous", there is always a certain amount of latency from the point the action is performed and the display shows the result of that action. There are several reasons for this. To start with, when you press a button, or otherwise activate an input device, it takes a certain amount of time for that button press to be transmitted to the processor (it may be less than a millisecond (ms) with a wired controller or as much as 10-20 ms when some wireless controllers are used, or if several are in use at once). Next, the processor needs time to process the button press. So, even if the processor responds right away to a button action, and moves the robotic arm, it may not do so for 17-33 ms or more, and it may take another 17-33 ms or more for the video capture at the surgical site to reflect the result of the action.

Depending on the system, the graphics hardware, and the particular video monitor, there may be almost no delay, to several frame times of delay. Since the data is being transmitted over the cloud, there typically is some delay sending the data to other surgeons watching and/or participating in the surgical procedure.

So, in summary, even when the system is running on a local machine, there is always latency. The question is simply how much latency. As a general rule of thumb, if a surgeon sees a response within 80 ms of an action, not only will the surgeon perceive the robotic arm as responding instantaneously, but the surgeon's performance will likely be just as good as if the latency was shorter. And, as a result, 80 ms is the desired "latency budget" for the systems described herein. That is, the system, which can be an OnLive system, has up to 80 ms to: send a controller action from the surgeon's location, through the internet to an OnLive data center, route the message to the OnLive server that controls the robotic arms, have a processor on the robotic system calculate the next movement of the robotic arm, while simultaneously outputting video and, optionally, audio feeds, which can be compressed, route the optionally compressed feeds through the internet, then decompress the feed, if it was compressed, at the surgeon's video display. Ideally, this can be carried out at video feed rate of at least 60 fps, with HDTV resolution video, over a consumer or business internet connection.

Over Cable and DSL connections, OnLive is able to achieve this if the surgeon and the remote surgical site are located within about 1000 miles of the OnLive data center. So, through OnLive, a surgeon who is 1000 miles away from a data center can perform remote surgery, and display the results of the surgery on one or more remote video displays, running on a server in the data center. Each surgeon, whether it is the surgeon or surgeons performing the simulated surgical procedure, or one or more students observing the procedure, will have the perception as if the surgery were performed locally.

OnLive's Latency Calculations

The simplified diagram below shows the latencies encountered after a user's action in the home makes it way to an OnLive data center, which then generates a new frame of the video game and sends it back to the user's home for display. Single-headed arrows show latencies measured in a single direction. Double-headed arrows show latencies measured roundtrip.

Figure 8:
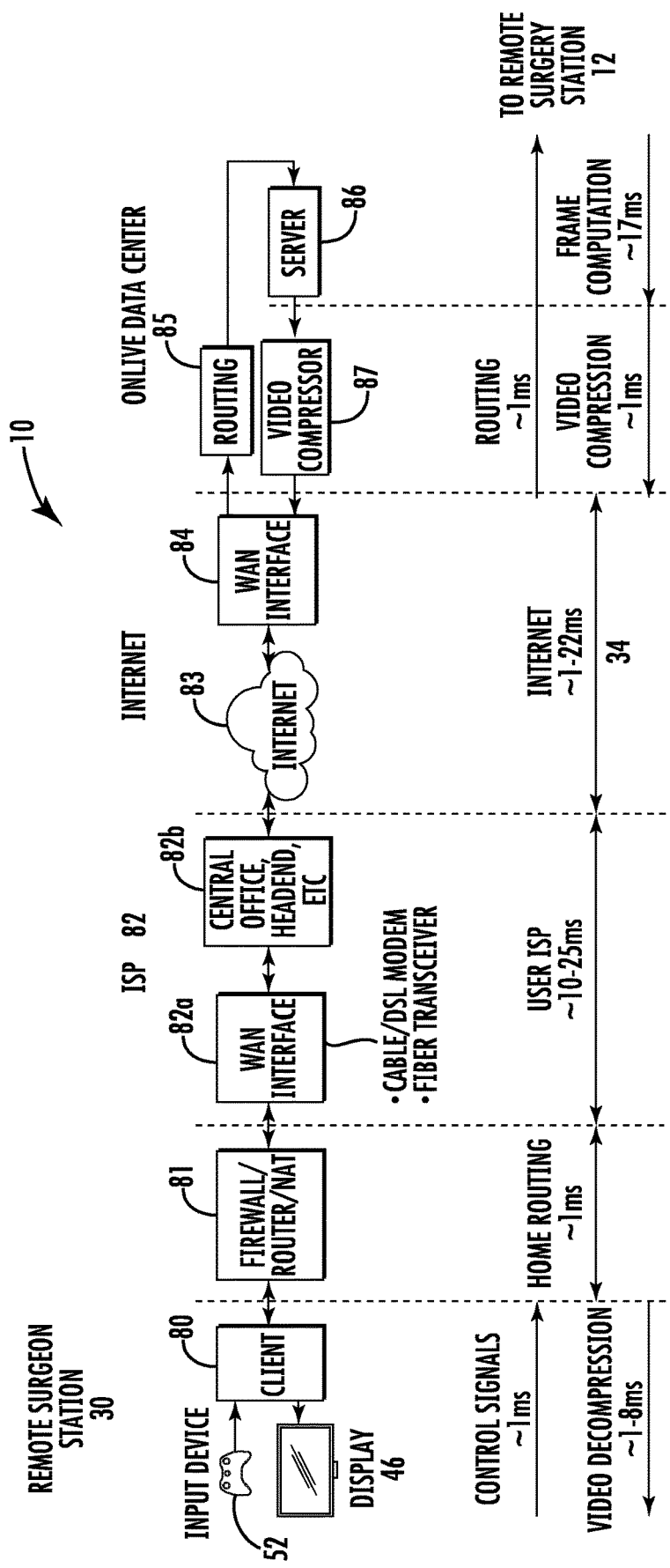
FIG. 8 shows an example of the flow of data to and from a surgeon to a surgical center, via an OnLive data center that may be used in accordance with a non-limiting example.

FIG. 8 shows the flow of data from the surgeon to the surgical center, via an OnLive data center. As illustrated in FIG. 8, the input device could correspond to a robotic surgeon station 30. The input device could be the controls 52 of FIG. 1 and connects to the client 80 with a connection to a firewall/router/NAT 81 and to the internet service provider 82 that includes a WAN interface 82a and a central office and head end 82b. It connects to the internet 83 and a WAN interface 84 that in turn connects to the OnLive data center with a routing center 85 including a router that connects to a server 86 and video compressor 87. At the client 80 video decompression occurs. This type of system is applicable for use with the telerobotic surgery system.

ISP Latency

Potentially, the largest source of latency is the "last mile" latency through the user's Internet Service Provider (ISP). This latency can be mitigated (or exacerbated) by the design and implementation of an ISP's network. Typical wired consumer networks in the US incur 10-25 ms of latency in the last mile, based on OnLive's measurements. Wireless cellular networks typically incur much higher last mile latency, potentially over 150-200 ms, although certain planned 4G network technologies are expected to decrease latency. Within the internet, assuming a relatively direct route can be obtained, latency is largely proportional to distance, and the roughly 22 ms worst case round-trip latency is based on about 1000 miles of distance (taking into account the speed of light through fiber, plus the typical delays OnLive has seen due to switching and routing through the internet.

Ideally, the data center and surgical center that are used will be located such that they are less than 1000 miles from each other, and from where a surgeon will be remotely accessing the robotic system. The compressed video, along with other required data, is sent through the internet back and forth from the surgeon to the robotic system. Notably, the data should be carefully managed to not exceed the data rate of the user's internet connection, as such could result in queuing of packets (incurring latency) or dropped packets.

Video Decompression Latency

Once the compressed video data and other data is received, then it is decompressed. The time needed for decompression depends on the performance of the system, and typically varies from about 1 to 8 ms. If there is a processing-constrained situation, the system will ideally will select a video frame size which will maintain low latency.

The system typically also includes controllers coupled to the articulate arms by a network port and one or more interconnect devices. The network port may be a computer that contains the necessary hardware and software to transmit and receive information through a communication link in a communication network.

The control units can provide output signals and commands that are incompatible with a computer. The interconnect devices can provide an interface that conditions the signals for transmitting and receiving signals between the control units and the network computer.

It is to be understood that the computer and/or control units can be constructed so that the system does not require the interconnect devices. Additionally, the control units may be constructed so that the system does not require a separate networking computer. For example, the control units can be constructed and/or configured to directly transmit information through the communication network.

The system can include a second network port that is coupled to a robot/device controller(s) and the communication network. The device controller controls the articulate arms. The second network port can be a computer that is coupled to the controller by an interconnect device. Although an interconnect device and network computer are described, it is to be understood that the controller can be constructed and configured to eliminate the device and/or computer.

The communication network can be any type of communication system including but not limited to, the internet and other types of wide area networks (WANs), intranets, local area networks (LANs), 'public switched telephone networks (PSTN), integrated services digital networks (ISDN). It is preferable to establish a communication link through a fiber optic network to reduce latency in the system. Depending upon the type of communication link selected, by way of example, the information can be transmitted in accordance with the user datagram protocol/internet protocol (UDP/IP) or asynchronous transfer mode/ATM Adaptation Layer 1 (ATM/AAL1) network protocols. The computers 140 and 150 may operate in accordance with an operating system sold under the designation VxWorks by Wind River. By way of example, the computers can be constructed and configured to operate with 100-base T Ethernet and/or 155 Mbps fiber ATM systems.

A mentor control unit can be accompanied by a touchscreen computer and an endoscope interface computer 158, where the touchscreen computer can be a device sold by Intuitive under the trademark HERMES. The touchscreen allows the surgeon to control and vary different functions and operations of the instruments. For example, the surgeon may vary the scale between movement of the handle assemblies and movement of the instruments through a graphical user interface (GUI) of the touchscreen. The touchscreen may have another GUI that allows the surgeon to initiate an action such as closing the gripper of an instrument.

The endoscope computer may allow the surgeon to control the movement of the robotic arm and the endoscope. Alternatively, the surgeon can control the endoscope through a foot pedal (not shown). The endoscope computer can be, for example, a device sold by Intuitive under the trademark SOCRATES. The touchscreen and endoscope computers may be coupled to the network computer by RS232 interfaces or other serial interfaces.

A control unit can transmit and receive information that is communicated as analog, digital or quadrature signals. The network computer may have analog input/output (I/O), digital I/O and quadrature interfaces that allow communication between the control unit and the network. By way of example, the analog interface may transceive data relating to handle position, tilt position, in/out position and foot pedal information (if used). The quadrature signals may relate to roll and pan position data. The digital I/O interface may relate to cable wire sensing data, handle buttons, illuminators (LEDs) and audio feedback (buzzers).

The position data is preferably absolute position information. By using absolute position information the robotic arms can still be moved even when some information is not successfully transmitted across the network. If incremental position information is provided, an error in the transmission would create a gap in the data and possibly inaccurate arm movement. The network computer may further have a screen and input device (e.g. keyboard) that allows for a user to operate the computer.

On the "patient" side, there is also a network and control computer. The controller may include separate controllers. The controller can receive input commands, perform kinematic computations based on the commands, and drive output signals to move the robotic arms and accompanying instruments to a desired position. The controller can receive commands that are processed to both move and actuate the instruments. Controller can receive input commands, perform kinematic computations based on the commands, and drive output signals' to move the robotic arm and accompanying endoscope.

Controllers can be coupled to the network computer by digital I/O and analog I/O interfaces. The computer may be coupled to the controller by an RS232 interface or other serial type interfaces. Additionally, the computer may be coupled to corresponding RS232 ports or other serial ports of the controllers. The RS232 ports or other serial ports of the controllers can receive data such as movement scaling and end effector actuation.

The robotic arms and instruments contain sensors, encoders, etc. that provide feedback information including force and position data. Some or all of this feedback information may be transmitted over the network to the surgeon side of the system. By way of example, the analog feedback information may include handle feedback, tilt feedback, in/out feedback and foot pedal feedback. Digital feedback may include cable sensing, buttons, illumination and auditory feedback. The computer can be coupled to a screen and input device (e.g. keyboard). Computers can packetize the information for transmission through the communication network. Each packet may contain two types of data, robotic data and other needed non-robotic data. Robotic data may include position information of the robots, including input commands to move the robots and position feedback from the robots. Other data may include functioning data such as instrument scaling and actuation.

Because the system transmits absolute position data the packets of robotic data can be received out of sequence. This may occur when using a UDP/IP protocol which uses a best efforts methodology. The computers are constructed and configured to properly treat any "late" arriving packets with robotic data. For example, the computer may sequentially transmit packets 1, 2 and 3. The computer may receive the packets in the order of 1, 3 and 2. The computer can disregard the second packet. Disregarding the packet instead of requesting a re-transmission of the data reduces the latency of the system. It is desirable to minimize latency to create a "real time" operation of the system.

It is preferable to have some information received in strict sequential order. Therefore the receiving computer will request a re-transmission of such data from the transmitting computer if the data is not errorlessly received. The data such as motion scaling and instrument actuation must be accurately transmitted and processed to insure that there is not an inadvertent command.

The computers can multiplex the RS232 data from the various input sources. The computers can have first-in first-out queues (FIFO) for transmitting information. Data transmitted between the computer and the various components within the surgeon side of the system may be communicated, for example, through a protocol provided by Intuitive under the name HERMES NETWORK PROTOCOL (HNP) Likewise, information may be transmitted between components on the patient side of the system in accordance with HNP.

In addition to the robotic and non-robotic data, the patient side of the system will transmit video data from the endoscope camera. To reduce latency in the system, the video data can be multiplexed with the robotic/other data onto the communication network. The video data may be compressed using conventional JPEG, etc., compression techniques for transmission to the surgeon side of the system.

Either computer can be used as an arbitrator between the input devices and the medical devices. For example, one computer can receive data from both control units. The computer can route the data to the relevant device (e.g. robot, instrument, etc.) in accordance with the priority data. For example, control unit may have a higher priority than control unit. The computer can route data to control a robot from control unit to the exclusion of data from control unit so that the surgeon at has control of the arm.

As an alternate embodiment, the computer cam be constructed and configured to provide priority according to the data in the SOURCE ID field. For example, the computer may be programmed to always provide priority for data that has the source ID from a control unit. The computer may have a hierarchical tree that assigns priority for a number of different input devices.

Alternatively, the computer can function as the arbitrator, screening the data before transmission across the network. The computer may have a priority scheme that always awards priority to one of the control units. Additionally, or alternatively, one or more of the control units may have a mechanical and/or software switch that can be actuated to give the console priority. The switch may function as an override feature to allow a surgeon to assume control of a procedure.

In operation, the system initially performs a start-up routine, typically configured to start-up with data from the consoles. The consoles may not be in communication during the start-up routine of the robotic arms, instruments, etc. therefore the system does not have the console data required for system boot. The computer may automatically drive the missing console input data to default values. The default values allow the patient side of the system to complete the start-up routine. Likewise, the computer may also drive missing incoming signals from the patient side of the system to default values to allow the control units to boot-up. Driving missing signals to a default value may be part of a network local mode. The local mode allows one or more consoles to "hot plug" into the system without shutting the system down.

Additionally, if communication between the surgeon and patient sides of the system are interrupted during operation the computer will again force the missing data to the last valid or default values as appropriate. The default values may be quiescent' signal values to prevent unsafe operation of the system. The components on the patient side will be left at the last known value so that the instruments and arms do not move.

Once the start-up routines have been completed and the communication link has been established the surgeons can operate the consoles. The system is quite useful for medical procedures wherein one of the surgeons is a teacher and the other surgeon is a pupil. The arbitration function of the system allows the teacher to take control of robot movement and instrument actuation at any time during the procedure. This allows the teacher to instruct the pupil on the procedure and/or the use of a medical robotic system.

Additionally, the system may allow one surgeon to control one medical device and another surgeon to control the other device. For example, one surgeon-may move the instruments while the other surgeon moves the endoscope, or one surgeon may move one instrument while the other surgeon moves the other instrument. Alternatively, one surgeon may control one arm(s), the other surgeon can control the other arm(s), and both surgeons may jointly control another arm.

One or more of the control units can have an alternate communication link. The alternate link may be a telecommunication network that allows the control unit to be located at a remote location while control unit is in relative close proximity to the robotic arms, etc. For example, control unit may be connected to a public phone network, while control unit is coupled to the controller by a LAN. Such a system would allow telesurgery with the robotic arms, instruments, etc. The surgeon and patient sides of the system may be coupled to the link by network computers.

The control system can allow joint control of a single medical instrument with handles from two different control' units. The control system can include an instrument controller coupled to a medical instrument. The instrument controller can minimize the error between the desired position of the medical instrument and the actual position of the instrument.

In some embodiments, a patient has image data scanned into the system, and during a simulation or a real surgery operation, a portion of the display screen shows a pre-recorded expert simulation via video tape, CDROM, etc., or a real-time tutorial by another doctor.

Telesurgery can be performed, in which a surgeon moves an input device (e.g., a full-size virtual scope or instrument) of a simulator while a robot actually performs a real operation based on the simulated motions of a surgeon at a remote location.

Telesurgery can be used in a teaching or testing embodiment, in which the virtual surgery device or other testing device questions via text and specific task questions. For example, in a medical embodiment, the virtual device might ask a test taker to go to a particular location in the anatomy and then perform a biopsy. Questions may be inserted in the test before, during or after a particular operation (such as a bronchoscopy). A multitude of tasks may be required of a student during the test procedure. The test taker may choose between different modes, such as an illustration, practice or exam mode.

In a typical operating room or training facility, several high-resolution video monitors are placed such that the surgical team can see the operation from the perspective of the operating surgeon (usually presented as a conventional 2-D image) as well as see the screen displaying the vital signs of the patient. Frequently, there are cameras positioned to record the entire operating theater to show to relative positions of the key players, such as anesthesiologists, nurses, physician assistants and training residents.

In training systems that do not use real animal tissue, computer-rendered images are displayed in lieu of actual tissue to represent the target of the surgical procedure. These images can be made to look extremely life-like. However, a trained medical professional can instantly distinguish between a computer-generated image of an operation versus a real operation performed on either living or non-living real tissue. The computer-generated image, however well-executed and made to appear as if it were moving, lacks the inherent differences that exist between multiple examples of real animals, such as those based on genetic diversity within the same species or even within the same litter.

The computer-generated image can offer substantial benefits in the training process in the same way that a well-drawn picture of an anatomical feature can help guide a surgeon to identify specific structures during the operation and during the pre- and post-operative imaging process. Specifically, drawing or rendering an anatomical feature or structure, without the naturally-occurring bleeding and spatial contortion sometimes present due to the viewing angle or viewing access, can offer a student substantial "clarity" and allow the student to learn how to translate the images found in an anatomy atlas such as Gray's Anatomy.

In one embodiment of the telerobotic simulation system described herein, the video image of the operation as seen by the surgeon (performed on animated real animal tissue) is shown on part of the "screen" (field of view) and, can be supplemented by showing a computer-generated image (still or motion video) which can presented into the field of view as a separate image or superimposed and scaled over the image of the real tissue. Additionally, other instructional material can be presented into the surgeon's field of view which can contain useful information about the operation, the tools used, other metrics of performance or information about specific products, chemicals, pharmaceuticals or procedures that may be placed in the field of view of the surgeon to derive advertising benefit, as the law allows.

The composite image that is seen in the field of view of the surgeon may be displayed onto the video monitors in the operating theater, or, the monitors may display information that supplements the training experience, such as instructional video material regarding safety issues or a checklist of items that must be present and accounted for prior to the surgery training experience beginning. For educational and study purposes, all audio and video generated from each source may be time synchronized and recorded.

As a result of students tests, reports may be issued relating to the experience a particular student had during the test, how well they did, in comparison to the correct procedures with the individual's performance, and an indication of the performance of all individuals taking these tests for a particular question. In this manner, an exam can be determined and customized for a particular company, for example. In another embodiment, the Medical Examination Board can identify different test questions by case, one time individual performance, cumulative performance by an individual, etc., and can provide different levels of difficulty. The virtual surgery system of the present invention or other test taking device not related to surgery or medical applications can include training, test taking and records archiving abilities (for example, in a medical context this archiving can relate to a patient's medical records).

In an embodiment, it is possible to use live patients and telerobotic surgery. As latency issues are solved, this becomes possible.

All references referred to herein are hereby incorporated by reference for all purposes.

Figure 12:
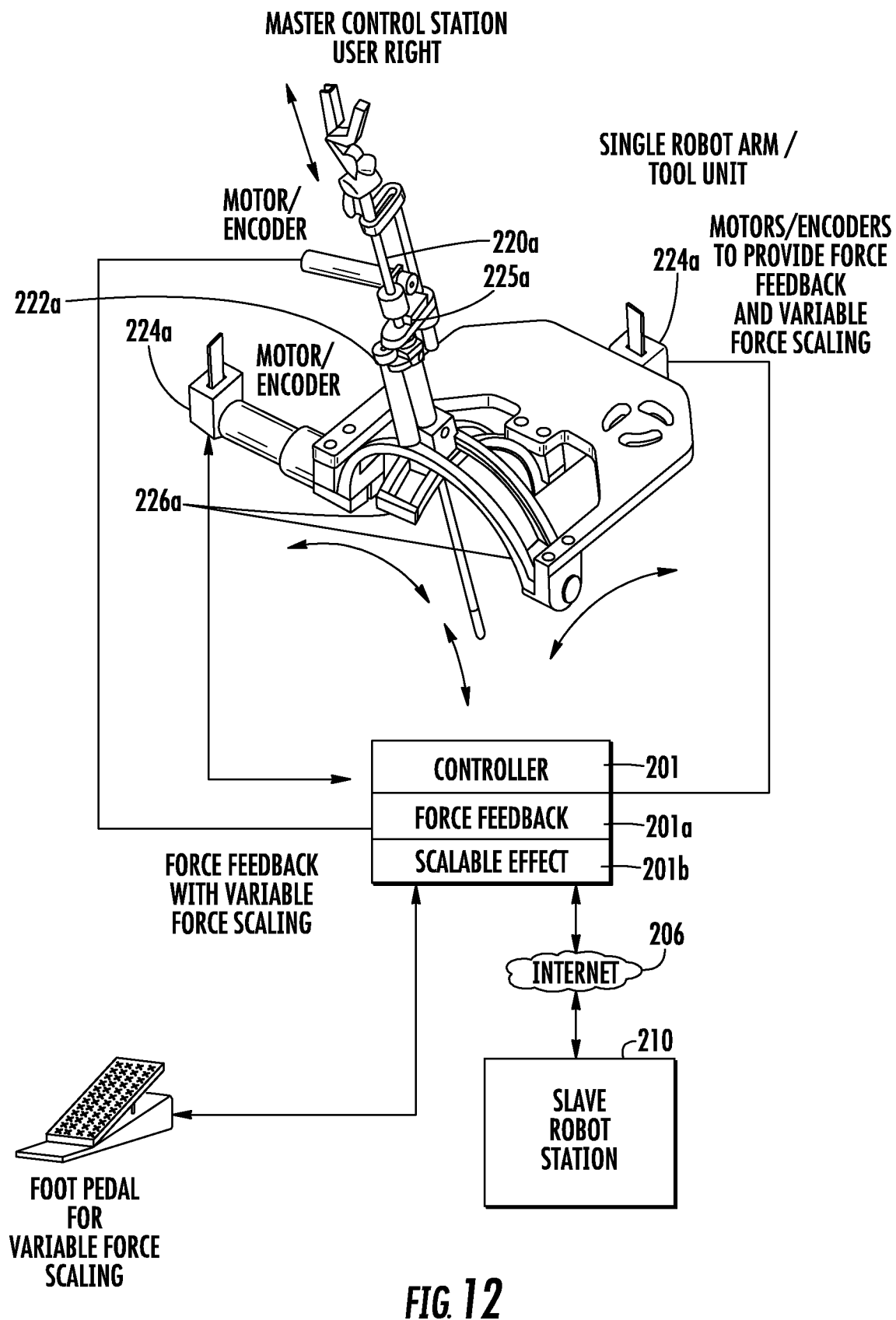
FIG. 12 is an isometric view of a robot arm and laparoscopic tool in accordance with a non-limiting example.
Figure 13:
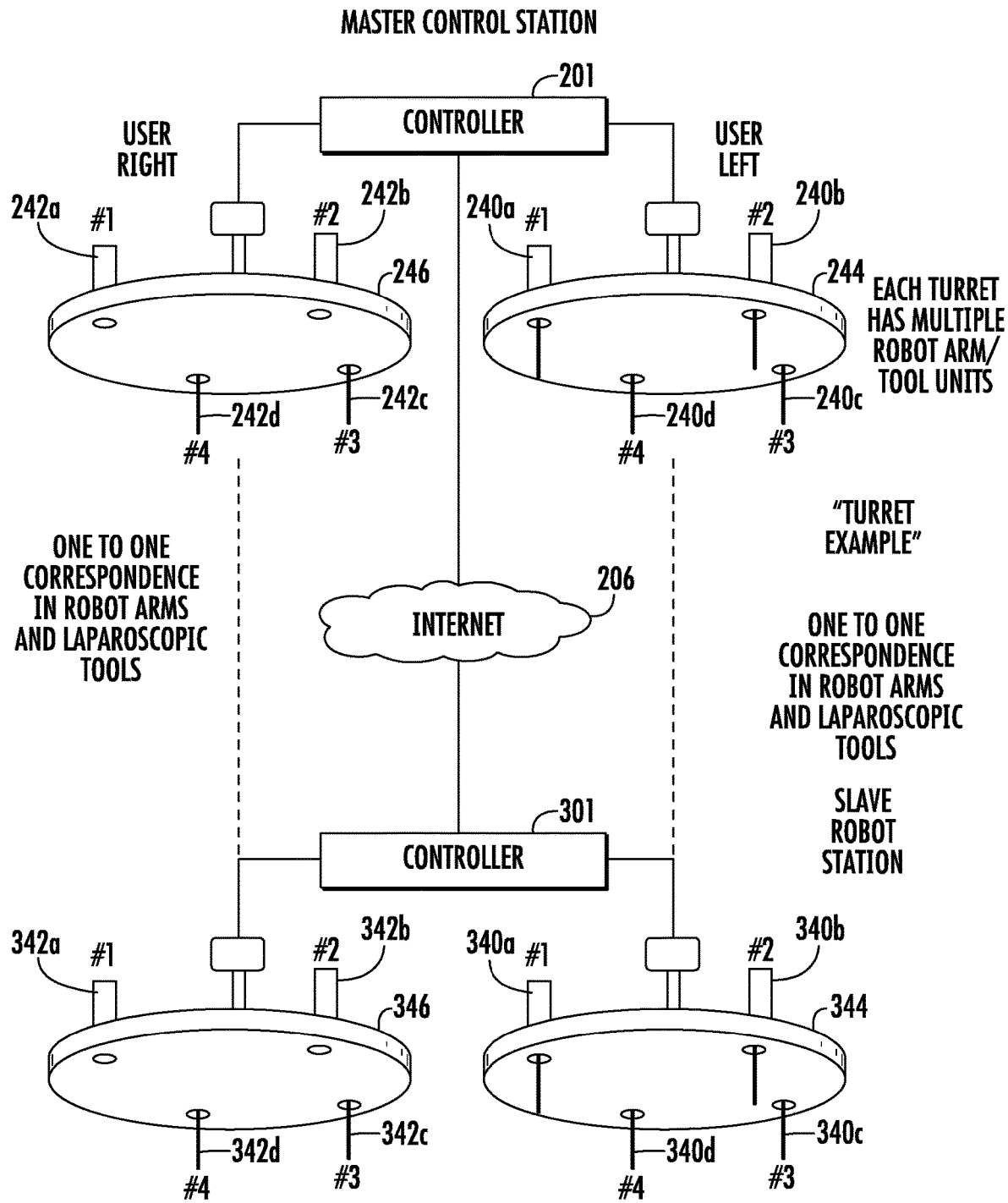
FIG. 13 is a fragmentary, block diagram view of a master/slave system having turrets at the master control station and slave robot station with left and right turrets each carrying four robot arms and associated laparoscopic tools that work in conjunction with each other in accordance with a non-limiting example.
Figure 14:
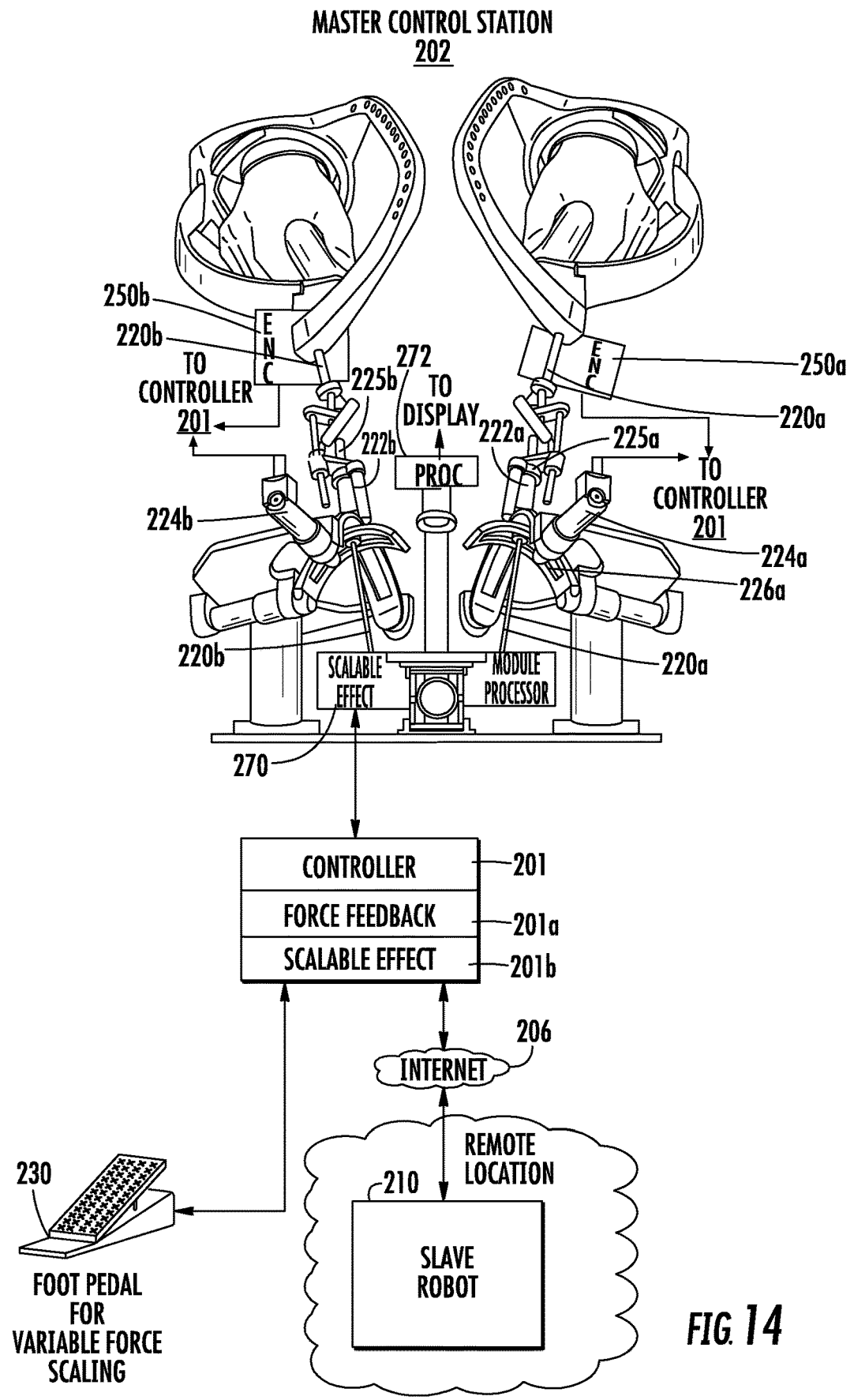
FIG. 14 is a fragmentary, perspective view of the master control station showing greater details of the robot arms and example laparoscopic tools in accordance with a non-limiting example.
Figure 15:
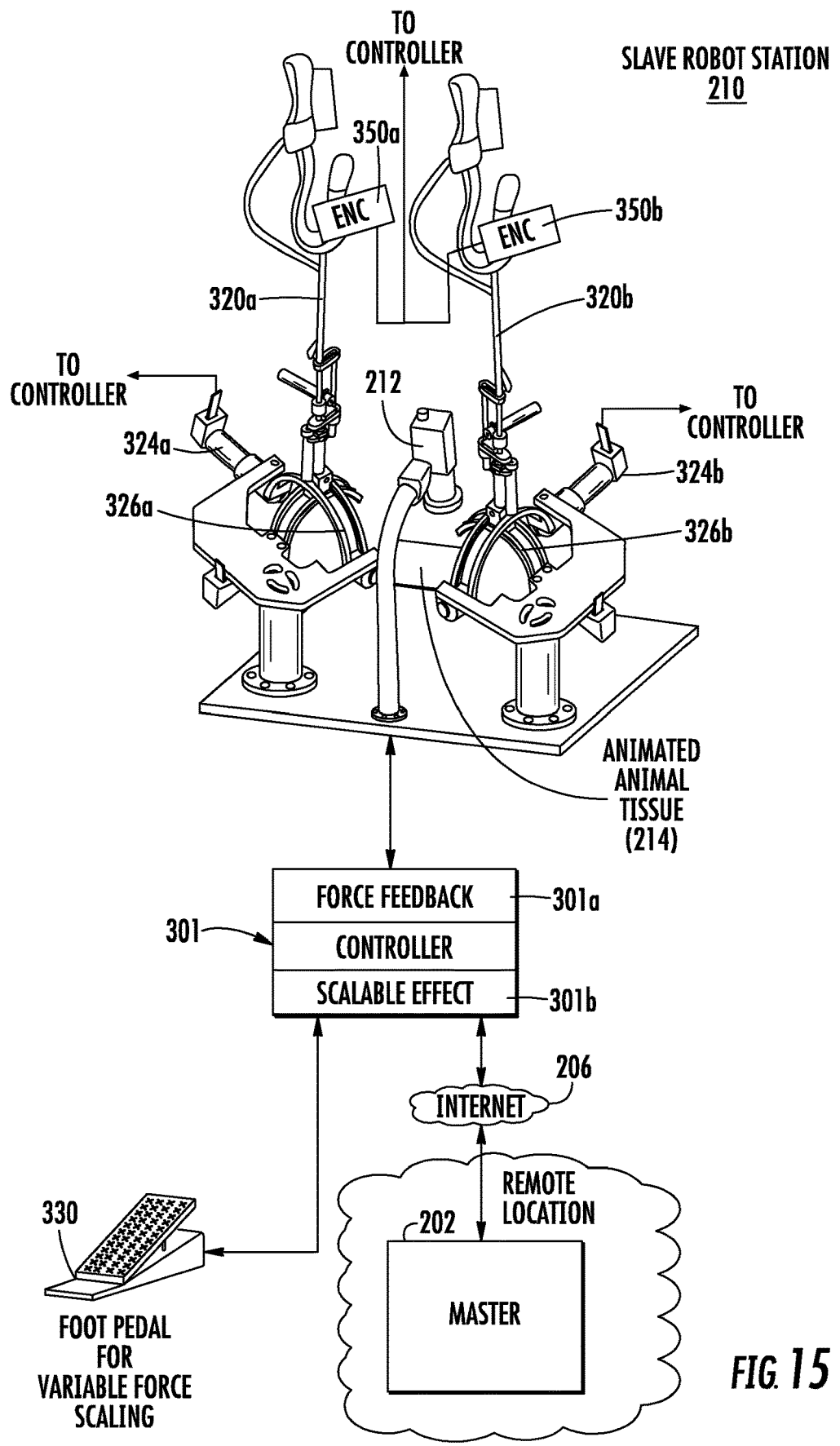
FIG. 15 is a fragmentary, perspective view of the slave robot station showing greater details of the robot arms and example laparoscopic tools in accordance with a non-limiting example.

Referring now to FIGS. 9-15, there are illustrated details of the modified laparoscopic surgical robot system that incorporates the modified tele-operated robot system having a master control station and slave robot station as described by the Advance Robotics article entitled, "Laparoscopic Surgical Robot for Remote In Vivo Training" as incorporated by reference above, and a minimally invasive surgical tool that is modified as a wrist joint simulation tool with enhanced dexterity and intuitive actuation as shown in FIGS. 14 and 15. The illustrated but modified wrist joint simulation tool is commonly referred to as the FlexDex™ and disclosed in the article from Awtar et al. entitled, "FlexDex™: A Minimally Invasive Surgical Tool With Enhanced Dexterity and Intuitive Actuation," Proceedings of the ASME, 2009 International Design Engineering Technical Conferences and Computers and Information in Engineering Conference, 2009, the disclosure which is hereby incorporated by reference in its entirety, and also disclosed in U.S. Pat. No. 8,668,702 to Awtar et al., and U.S. Patent Publication No. 2016/0256232 to Awtar et al., and U.S. Patent Publication No. 2016/0303734 to Bowles et al., the disclosures which are hereby incorporated by reference in their entirety.

The master/slave system as described below offers the surgeon the ability to modulate any haptic feedback signals to reduce or increase the amount of force the motors/encoders exert upon hand controls. This reduction of haptic force could help with certain repetitive motion disorders while increasing or decreasing the haptic force and help the surgeon navigate and discern different tissue types by heightening the feedback when required. The system may also use a mechanical laparoscopic tool that simulates the more expensive robotic systems and incorporate it with such master/slave system for training, but also providing not only haptic feedback, but modulation of that haptic feedback.

The master control station and the slave robot station may operate together similar as the remote surgeon station for the master control station and robotic surgery station for slave robot station as described above. The master/slave system operates as a Fundamentals of Laparoscopic Surgery evaluation platform and may operate together as a five Degree of Freedom master-slave pair of robotic manipulators that allows two users at two different physical locations to perform interactive teaching and learning in laparoscopic surgical procedures and cooperative telesurgery. Less experienced or new surgeons may be taught and/or guided through laparoscopic procedures via a more experienced master surgeon. The two stations may use commercially available laparoscopic tools such as conventional Karl Storz instrument housings, and more particularly, the robotic system incorporates the FlexDex™ minimally invasive surgical tool that is modified for use at both the master control station and slave robot station as shown in FIGS. 14 and 15 and explained in greater detail below. The robotic system also improves on the haptic force feedback and allows variable force scaling that provides the surgeon or student the ability to modulate the haptic feedback signals and reduce or increase the amount of force the motors/encoders exert upon hand controls to accommodate soft tissue or hard bone, etc. Reduction of the haptic force may help in certain repetitive motion disorders and increasing the haptic force could help the surgeon navigate and discern different tissue types by heightening the feedback when required.

The variable force scaling permits a "power steering" effect and allows the attenuation and amplification of the haptic signal coming back. This can be important during laparoscopic surgery such as when the tool is moved close to a vessel, but the surgeon desires to stop at the vessel. The surgeon may want to increase the sensitivity by reducing the amplification at that time, which could be advantageous since the increase in sensitivity reduces the chance of breaking the vessel, and thus, reduce the chance of blood loss. If the surgeon begins to cut through gristle or other hard material, the power or amplification can be increased to move through the harder material as compared to requiring the increased sensitivity near a blood vessel. This type of system is advantageous also with a laparoscopic tool such as the FlexDex™ or other laparoscopic tool having the long and narrow hollow rods with wires in them to the end effector where the wires can be connected near the point where the tube to the end effector begins and sensors and motors/encoders attached and permit force feedback with variable force scaling. Optical sensors can be used in those embodiments.

One particular advantage embodiment includes left and right turrets positioned at the left and right-hand side units of the master control station and similar left and right turrets at the slave robot station as will be explained in greater detail below. Each turret includes four robot arms with each robot arm having a specific laparoscopic tool. The turret may be rotated 90 degrees to select the robot arm and tool at the master control station with a similar incremental change mimicked in the slave robot station so that a particular robot arm and tool is selected. Each robot arm and laparoscopic tool has its own motors/encoders and sensors, and thus, four laparoscopic tools can be rotated, one at a time, into a position where the laparoscopic tools are selected to accommodate left and right-handed surgeons. This is advantageous since only one system needs to be shipped and there is no necessity for massive cleaning since the robot arm and its laparoscopic tool can be taken off and cleaned. This could be advantageous in embassies or consulates that may have operating rooms and triage facilities. It is advantageous to have a robot arm with the commercial variant of a laparoscopic tool positioned on the turret on either side forming the left and right-hand side units of the master control station and the slave robot station, allowing laparoscopic tools to be rotated in such as by 90 degree incremental rotation of the turret. A specific laparoscopic tool could be inserted by means of a trocar, the surgery accomplished, the laparoscopic tool pulled out, and the turret rotated to change the laparoscopic tool. The new laparoscopic tool is placed into the opening for surgery. In an example, there are four robot arms on the turret and they are rotated into a selected position. The overall system allows a surgeon to operate with a master control station and slave robot station permitting greater flexibility. The surgeon can even sit and lean back to relieve back strain since the stations are adaptable.

Figure 9:
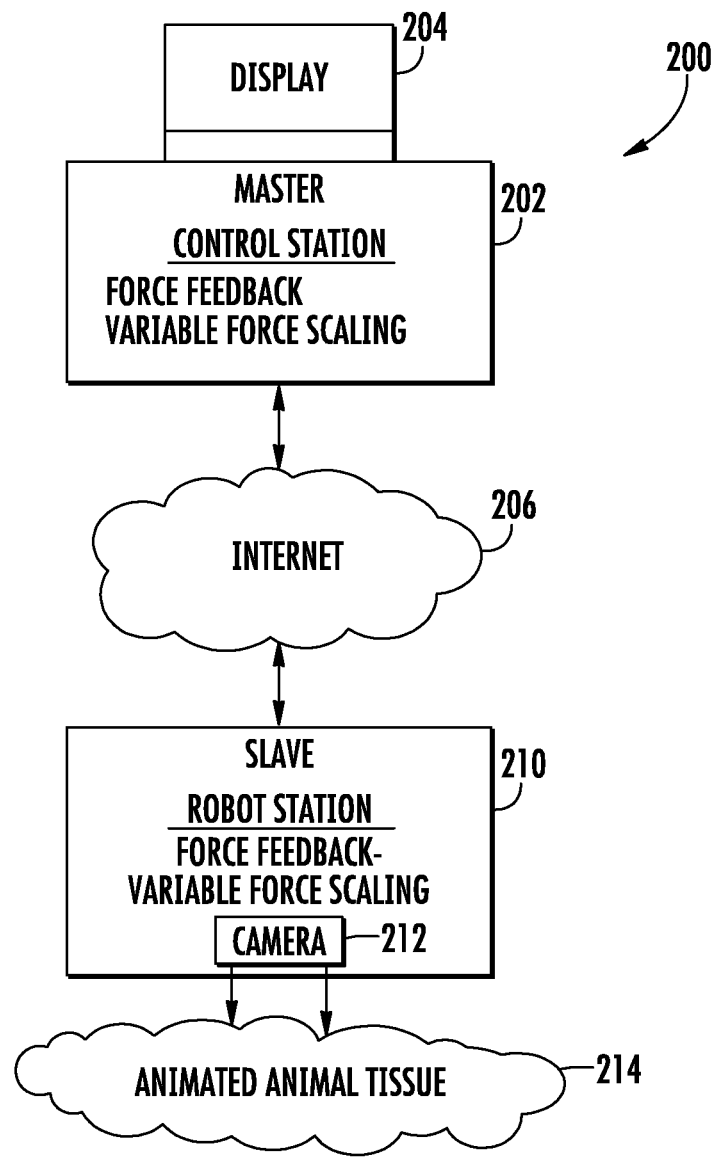
FIG. 9 is a fragmentary, block diagram showing basic components of the telerobotic surgery training system that includes a master control station and a slave robot station in accordance with a non-limiting example.

Referring now to FIG. 9, there is illustrated the master/slave robotic system 200 that includes a master control station 202 and associated display 204. The master control station 202 communicates via a communications network such as the internet 206 with a slave robot station 210 which includes a camera 212 that images animated animal tissue 214 located at the slave robot station. The master control station 202 operates with force feedback and a variable force scaling to increase or diminish the force feedback similar to "power steering" using associated sensors and motors/encoders and allow the user at the master control station to operate the slave robot station 210 while viewing the images of animated animal tissue via the camera 212. The tissue may be animated by techniques as described above. The master control station 202 may be located at a remote surgeon station at a second location in a second structure at a second geographic point, and the slave robot station 210 may be at a robotic surgery station at a first location in a first structure at a first geographic point. It should be understood that the master/slave robotic system 200 as described at FIGS. 9-15 with the combination of the master control station 202, slave robot station 210 and other laparoscopic tools, such as a wrist joint simulation tool as described in greater detail below and also referred to as the FlexDex minimally invasive surgical tool may be used in combination with all of the other features described above relative to FIGS. 1-8 and their description.

Figure 10:
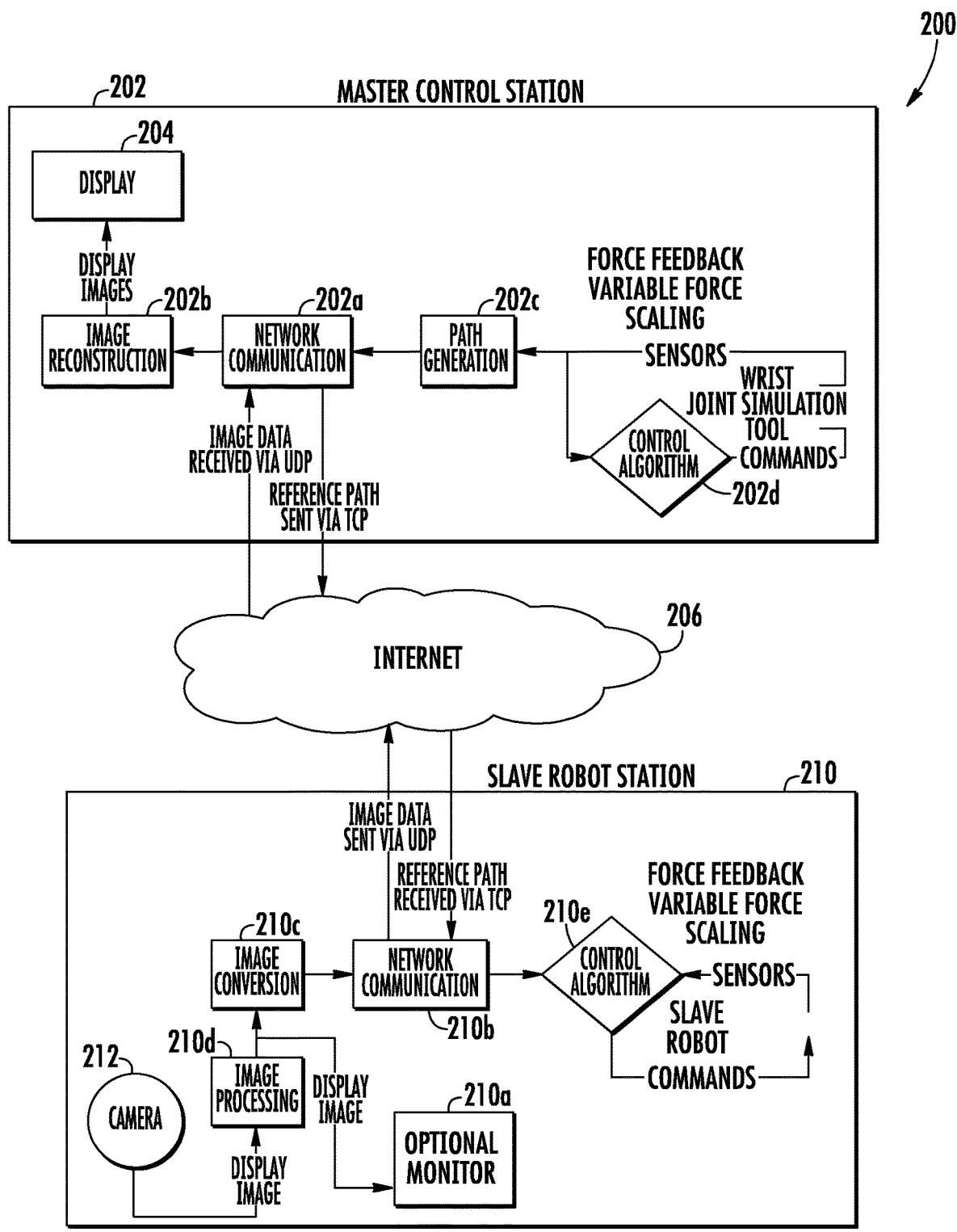
FIG. 10 is another more detailed block diagram of the master control station and slave robot station showing the flow of data in accordance with a non-limiting example.

FIG. 10 is a more detailed block diagram showing the master control station 202 and slave robot station 210 communicating via the communications network such as the internet 206 to each other and showing basic programming modules and components. As illustrated, the master control station 202 includes a network communication module 202a that receives image data from the slave robot station 210 via UDP and transmits reference data as a reference path for control over the slave robot station via TCP. The master control station 202 includes an image reconstruction module 202b that connects to the display 204 and a path generation module 202c that interoperates with a control algorithm 202d. Sensor data and the control algorithm data commands are sent and received to and from various mechanical components of the laparoscopic tools, including various sensors and motors/encoders as explained below. The image is reconstructed as obtained from the slave robot station 210 when viewing the animated animal tissue and displayed on the display 204. The slave robot system 210 receives reference path data via the TCP connection with the internet and image data is sent via UDP to the master control station in one non-limiting example. The camera 212 receives digital images that are processed and converted for network communication. The images may be displayed at an optional monitor 210a so that a student that is working at the slave robot station may also view what the master surgeon is viewing at the master control station. Data is received or transmitted via a network communication interface 210b and an image conversion module 210c interoperates with an image processing module 210d. Data is controlled via a control algorithm module 210e for force feedback variable force scaling. A control algorithm allows force feedback and variable force scaling at the slave robot station from the signals sent by the master control station when an operator such as a master surgeon or even a student is working at the master control station.

Figure 11:
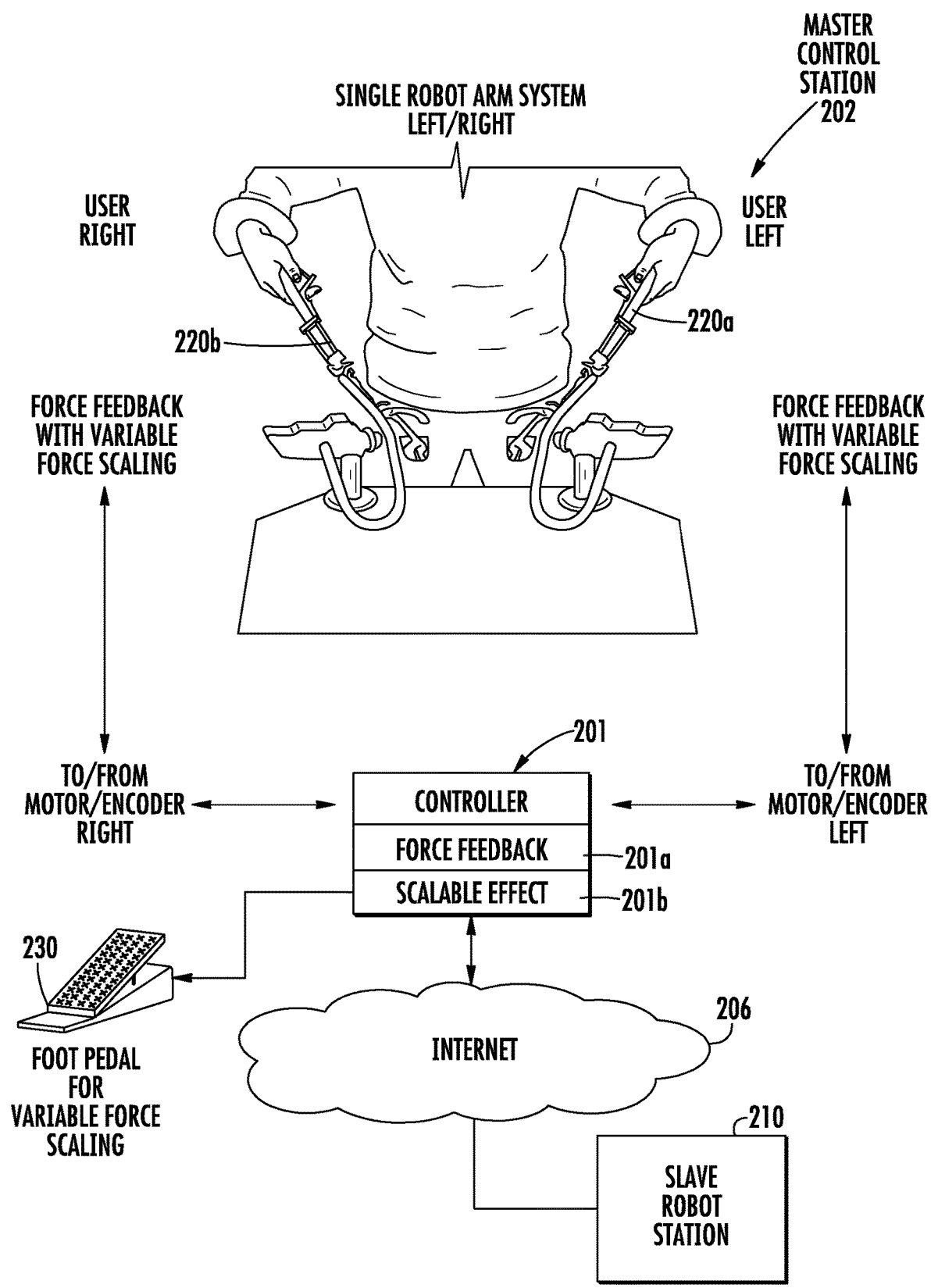
FIG. 11 is a partial perspective and fragmentary view of a user at the master control station manipulating left and right laparoscopic tools carried by left and right robot arms that are mimicked at the slave robot station in accordance with a non-limiting example.

Referring now to FIG. 11, there is illustrated further details of the master control station 202 and showing a user operating left and right laparoscopic tools 220a, 220b that are carried by the respective pair of left and right robot arms 222a, 222b with the respective drive motors/encoders (FIGS. 12 and 14) 224a, 224b attached to the robot arms and operative with their controller 201 as a second controller 201, which in turn connects to the slave robot station 210 via the internet 206. The controller 201 includes a force feedback module 201a to provide haptic feedback to the user at the laparoscopic tool being manipulated, and a variable force scaling module 201b configured to modulate the haptic feedback to a user and increase or decrease the effective tool movement felt by the user. The system includes appropriate sensors to allow force feedback with variable force scaling as explained above. The user grasps the respective laparoscopic tool and manipulates the laparoscopic tool by hand and signals are transmitted via the controller 201 to the slave robot station 210 where a similar set of robot arms carrying laparoscopic tools mimics the user manipulation of the laparoscopic tools at the master control station. The users manipulate single robot arm systems, each carrying in this example a single laparoscopic tool.

FIG. 12 is an isometric view of the left robot arm 222a with a laparoscopic tool 220a such as shown in FIG. 11. The respective tool holder 225a as part of the robot arm 222a is illustrated and supports the laparoscopic tool 220a to allow vertical movement. Arcuate arms 226a rotate on independent axes and have the appropriate motors/encoders 224a to move the tool holder 225a as part of the robot arm 222a on each arcuate arm 226a. The right side robot arm 222b has similar units and parts (FIG. 14). A foot pedal 230 connects to the controller 201 and provides variable force scaling. The slave robot station 210 will have similar components as shown in FIG. 15, but in the 300 series.

It is also possible to place four respective left and right robot arms with an attached laparoscopic tool as a unit on a respective turret such as shown in FIG. 13 so that a respective turret may be incremented 90 degrees and a specific laparoscopic tool selected. As shown in FIG. 13, the master control station 202 and slave robot station 210 each include left and right turrets 244, 344 and 246, 346. Each turret includes four robot arms 240a-d, 242a-d, 340a-d, 342a-d and each carrying a respective laparoscopic tool, such that each form the individual units such as shown in FIG. 12. As a turret 244, 246 is incremented at the master control station 202, likewise the turret 344, 346 having the corresponding robot arm and laparoscopic tool at the slave robot station is rotated into position so that the robot arms and laparoscopic tools are in one-to-one correspondence and tools may be selected depending on surgical needs.

Each turret 244, 246, 344, 346 may include respective individual robot arms 240a-d, 242a-d, 340a-d, 342a-d and laparoscopic tool units such as the types shown in FIG. 12 and indexed or incremented when necessary for surgical operation. Also, left and right-handed surgeons can be accommodated by a selection of tools that can be incremented. Although FIG. 13 is a schematic diagram, appropriate design modifications to the master/slave robot system are made to allow this turret example. A foot pedal may be used for the variable force scaling and positioned at each station. The feedback signal can be increased or decreased and the "feel" of the tool may be adjusted in the force feedback.

FIG. 14 shows greater details of the master control station 202 and shows an operator holding two laparoscopic wrist joint simulation tools 220a, 220b that are modified from the FlexDex tools and modified for use at this example of master control station 202. This system has five degrees-of-freedom (DoF) motion-control over these two laparoscopic wrist joint simulation tools 220a, 220b and a surgeon is shown manipulating the tools. The slave robot station 210 shown in FIG. 15 has two of the wrist joint simulation tools 320a, 320b station and similar components as described relative to the master control station but reference numerals given in the 300 series. Respective encoders 250a, 250b, 350a, 350b may be connected to each tool 220a, 220b, 320a, 320b and connected to respective controllers 201, 301 and provide encoded signals for tracking. Users at the two different physical locations can be remotely separated at two geographic locations and perform interactive teaching such as the tele-mentoring and interactive learning in laparoscopic procedures and provide cooperative telesurgery or practice such as on the animated animal tissue. Thus, the less experienced or new surgeon can be taught and/or guided through the different laparoscopic procedures.

As illustrated, the master control station 202 and slave robot station 210 each include the pairs of left and right arcuate arms 226a,b and 326a,b that rotate on independent axes. The wrist joint simulation tools 220a,b and 320a,b are held between the arms, and thus, held to a spherical surface. The tool holders 225a,b and 325a,b support the wrist joint simulation tools 220a,b and 320a,b at each arm to allow insertion, twist rotation and grasping that is tracked by motors/encoders 224a,b and 250a,b and 324a,b and 350a,b to indicate movement of the laparoscopic tool. The first controller 301 is at the slave robot station and second controller 201 is at the master robot station. Data from motors/encoders at the master robot station is processed by the controllers 201, 301, which process not only force feedback data, but also the data related to scalable effects and transmits data via the internet to the respective slave robot station 210 in which the first controller 301 at the slave robot station will duplicate the movements using its motors/encoders positioned on similar wrist joint simulation tools that are supported by the corresponding arcuate arms.

A foot pedal 230, 330 at each station may be operated at the master control station or at the slave robot station for variable force scaling so that via the controllers 201, 301, the feedback signal can be increased or decreased and the "feel" of the tool may be adjusted in the force feedback. There may be an increased feel of resistance such as when cutting through cartilage at the animated animal tissue and less of a feel of resistance if performing surgery on soft tissue.

As shown in FIG. 15, the slave robot station 210 may include animated animal tissue 214 (also shown in FIG. 9) that permits a student or surgeon in training to practice surgery on the tissue. An experienced surgeon could be located at the master control station 202 and as the student manipulates the tools located at the slave robot station 202, and in turn, the experienced surgeon can follow at the master robot station 202 and view the student or trainee surgeon's progress via the display 204 since video is taken at the slave robot station camera 212. The experienced surgeon could override the trainee surgeon and take active control.

This surgical system of both the master control station 202 and slave robot station 210 allows five degrees-of-freedom, i.e., roll, pitch, yaw, depth and grab. The use of the two arcs or arcuate arms permits a remote center at the geometric center of the spherical surface with an improved range of motion, i.e., a half-cone region with a 60 degree inclination measured from vertical and using appropriate servomotors for detailed movement. This spherical mechanism achieves three degrees-of-freedom as roll, yaw and pitch in a single joint and includes direct-drive connections for the servomotors or other drive motors. The other components permit insertion, twist-rotation and grasping with insertion allowing downward movement or upward movement of the tool using a friction drive configuration on urethane rollers and gear box-pinion and bevel gears.

The system as illustrated in FIGS. 14 and 15 includes the spherical mechanism of the arcs or arcuate arms, and may have a tool insertion mechanism that allows a transverse motion of the tools in conjunction with a rotation mechanism. A grasping mechanism may work in association with the wrist joint simulation tool and is modified for use with the master control station and slave robot station. A spherical support mechanism locates and guides the laparoscopic tool through the remote center of motion (RCM) using a pitch arc and roll arc as two-dimensional planar guides and form a spherical joint.

Any insertion mechanism may provide depth and linear motion to the modified wrist joint simulation tool. A surgeon's hand rotation may exert a normal force perpendicular to the AoR with the force exerted on a guide rail, for example, that causes a respective tool to rotate. A small set of sensors my track motion of the laparoscopic instruments, and in this example, the wrist joint simulation tools by the operator such as the surgeon at the master control station 202 so that the motions are encoded and data sent over the internet connection to the slave robot station 210 where the slave robot station receives the data and actuates motors/encoders so that its tools are moved and perform the same movements and functions identically as what occurs at the master control station 202. Thus, there is a one-to-one mapping motion between the surgeon movements located at the master control station and those instruments as the tools at the slave robot station 210.

The type of communication of control signals as data over the internet may vary, but in one example, data may be sent over a standard packet-switched internet connection from the master control station 202 to the slave robot station 210. Drive motors and sensors or encoders may be independent and use a separate packet stream as a control signal such that different control signals can be sent as separate UDP packet streams, each on a unique and preassigned port. At the master control station 202, the controller 201 may compute a one-byte checksum on each outgoing packet so that the controller 301 at the slave robot station 210 that receives the packets may detect corrupted packets and any corrupted, dropped, and out-of-order packets may be ignored. A millisecond time-stamp in each data packet may determine order. To reduce latency, UDP is selected over the TCP and avoid protocol-required automatic retransmission of lost or corrupted packets.

A live video stream may be captured at the slave robot station 210 where the camera images from the camera 212 of the animated animal tissue 214 may be sent via the first controller 301 and internet to the second controller 201 at the master control station 202. One example of a camera that may be used is a Storz Endoscope that provides a resolution of 768×494 pixels. Other cameras may be used as known to those skilled in the art. In one example, a closed-circuit video connection may be used or if not available, video may be encoded to different frames a second using standard techniques.

In the examples of FIGS. 14 and 15, both the master control station 202 and the slave robot station 210 include the wrist joint simulation tools 220a,b and 320a,b as the FlexDex™ that is modified to be carried by and work with each of the manipulators or robot arms. This type wrist joint simulation tool approximates the flexure and wrist action of the most advanced robotic assisted surgery devices such as the Intuitive Surgical, DaVinci robot system. In its modified version for use with the master/slave robotic system as described, the FlexDex™ tool is opened at the point where the handle ends but joins the shaft, and each of the flexible wires that feed to the end effector is intercepted with a separate motor/encoder and sensor (such as optical sensor) such as shown by the block diagram 270 as shown in FIG. 14 and labeled scalable effect module processor 270 and operatively connected to each wrist joint simulation tool 220a,b. In operation with the controller 201, this may aid to provide the force feedback with variable force scaling. Any laparoscopic tool having a similar shaft and wires may be appropriately modified. The block diagram is representative of several motors/encoders connected to respective wires of the FlexDex™ tool. The motors/encoders are mounted to the arm and capture the motion in the cone above the entry point to the abdomen or chest wall and individual wires in the shaft can be modulated separately or collectively as could the rotation of motion within the cone. The entire assembly may be fitted and/or mounted, and this allows a surgeon to sit down during surgery or training and low-pass software filters can be applied that would filter out hand tremors and smooth out the motion of the end effectors.

Each of the wrist joint simulation tools 220a, 220b and 320a, 320b may include a rigid frame that is secured to the surgeon's forearm via an arm brace as shown in FIG. 14 such that the tool frame and the surgeon's forearm provides a common ground reference. In a real life surgical experience, the tool shaft would pass through a surgical port in the patient's body during an operation and extend from that tool frame, but is intercepted by motors/encoders that connect to the second controller 201 at the master control station and at the slave robot station 210 with a similar arrangement. The surgeon's forearm motions are tracked along the four degrees-of-freedom (DoF) with three translations and one roll rotation that may be imparted to the end of the tool shaft and reproduced at the slave robot station.

At the master control station 202 in one embodiment, the tool shafts are inserted into the scalable effect module and processor 270 in this non-limiting example. Other systems may be used. The surgeon looking at the display via a display processor 272 will be able to move the tool, and in effect, with the motors/encoders and tracking with the scalable effect module 270 and track the surgeon's movements and have a corresponding movement at the slave robot station where the wrist joint simulation tools are similarly mounted on the robot arms and moved. The movement is caught on camera and displayed at the display of the master control system. The surgeon may hold a tool handle that is connected to the tool frame using a virtual center (VC) mechanism as described above that creates a virtual center of rotation for the tool handle that coincides with the surgeon's wrist, and thus, the surgeon's hand may move freely and naturally about the surgeon's wrist when operating the tool. Any cables run through the hollow tool frame and transmit two additional wrist degrees of freedom as yaw and pitch rotation to the surgeon's hand and to the end-effector via the break in the tool and modified connection to the motors/encoders. It should be understood that the scalable effect module and processor 270 may not be required if the motors/encoders sense movement that is registered into the slave robot station 210 and duplicate one-to-one corresponding movement via any motors/encoders at the slave robot station.

Any virtual center mechanism produces a virtual center of rotation for the tool handle that coincides with the user's wrist to enable a natural and intuitive actuation of two wrist-like rotations of the end-effector. Different designs may be used and reference is made to the incorporated by reference FlexDex article by Awtar et al. and the incorporated by reference '702 patent and incorporated by reference '734 and '232 patent publications identified above. Different foot pedals can be used for variable force scaling, but one possible design is a foot pedal design where the amount of force scaling either up or down is determined by the amount of user depression of the pedal. The user may switch between either amplifying the signal when depressing the pedal or minimizing the signal when depressing the pedal, and thus, change the variable force scaling.

Figure 16:
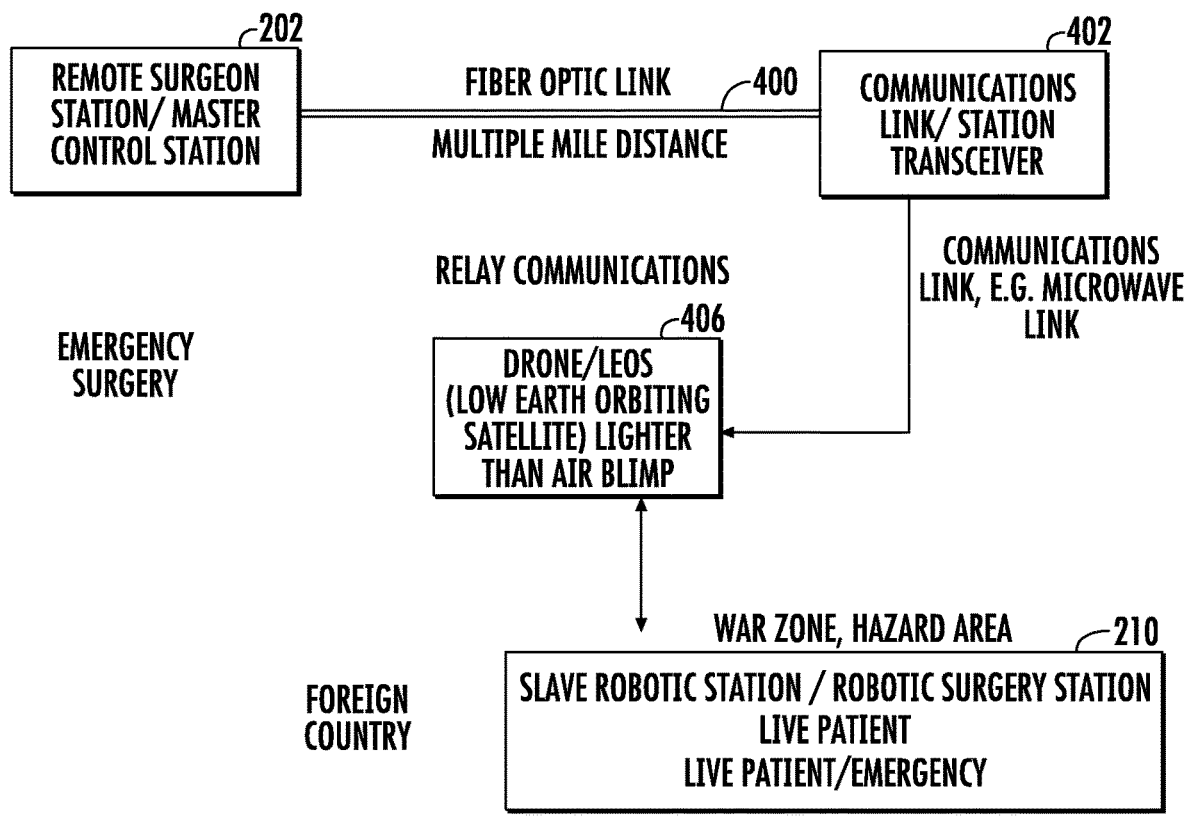
FIG. 16 is a block diagram of the master control station and a relay communications link to a robotic surgery station for live patient treatment such as a warzone in a foreign country in accordance with a non-limiting example.

It is possible to modify the master/slave robotic surgery system 200 for emergency situations and operate on live patients such as the robot system shown in FIG. 16. A fiber optic link 400, for example, connects over a distance of a few miles or even hundreds or thousands of miles to a communications link/station 402 that may be a transceiver that is close to or in the war zone or hazard area where a live patient requires emergency assistance. A surgeon could be located remotely at a surgeon station that includes a surgeon console similar to the master control station as described above or with modifications. The communications link/station includes a transceiver that may communicate via microwave or other communications signal to a drone, LEOS (low earth orbiting satellite) or light-than-air-blimp 406 as non-limiting examples. The remote surgeon operates at this modified master control station 202 and receives video images of the live patient from a video camera located at this modified slave robot station 210. The video images are transmitted back to the master control station 202 via the relay communications link 402, 406 that may include the drone, LEOS or lighter-than-air-blimp or other communications device to allow the remote surgeon to receive the video images. The remote surgeon is located at his surgical console at the remote surgeon station operating as a master control station and manipulates his tools or other controls, and in turn, directs the robot arms at the slave robot station to operate or assist medical personnel that are already present. The slave robot station includes one or more robot arms carrying surgical tools such as at least one laparascopic tool or other surgical tool that is controlled by the remote surgeon.

It is possible to have the remote surgeon assist medical personnel at the war zone or hazardous area by assisting medical personnel on a robot machine. The latency of the communications between the master control station 202 and slave robot station 210 can be easily checked even on site using a laptop computer, Ipad or similar portable device to ensure the communications connection is adequate and does not suffer undue delay. Appropriate communications security may be implemented. If it is determined that latency, security or speed become problematic issues with one selected communications link, then another communication link can be selected as long as it is adequate and does not suffer from the latency, security or speed issues of the previous link. Such robotic system as described could also be used with live pigs or other animals besides live humans and also be used on animal tissue. Latency can be critically important with live patients and it is preferred for latency to be not greater than 200 milliseconds in one example, not greater than 140 milliseconds in another example and even less in yet other examples.

An example situation could be an embassy in a remote foreign country having an emergency care or operating room that includes a slave robot station or similar device and an emergency occurs where a live patient must be treated. A similar example could be where a live patient needs treatment a few miles from the embassy and a small but somewhat portable slave robot station is moved adjacent the live patient requiring treatment. The communications link is established with the remote surgeon via the high speed fiber optic link to the embassy. A drone may be circling the location a few miles or more away from the embassy near the live patient and receive from the embassy microwave signals carrying data from the remote surgeon station to assist surgery or control the slave robot station. Other modifications can be made as necessary.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A telerobotic surgery system for remote surgeon training, comprising:
    a robotic surgery station having a first pair of robot arms, each carrying a laparoscopic tool and each having a robot arm drive, and a first controller connected to each robot arm drive and controlling movement of the pair of robot arms and respective laparoscopic tool;
    harvested animal tissue at the robotic surgery station;
    a remote surgeon station having a second pair of robot arms, each carrying a laparoscopic tool and each having a robot arm drive, and a second controller connected to each robot arm drive at the remote surgeon station that receives data regarding movement of the second pair of robot arms and respective laparoscopic tool based on user manipulation of each laparoscopic tool at the remote surgeon station;
    a communications network coupling said first and second controllers, wherein the second controller at the robotic surgery station is operative as a master to communicate data to the first controller regarding user manipulation of the second pair of robot arms and respective laparoscopic tool, wherein the first controller is configured to control each robot arm drive and effect one-to-one movement of the first pair of robot arms and carried laparoscopic tools as a slave based on user manipulation of each laparoscopic tool at the remote surgeon station; and a left turret and right turret positioned at each of the robotic surgery station and remote surgeon station, each left and right turret supporting a plurality of robot arms, each robot arm having a laparoscopic tool and each having a robot arm drive and connected to the respective controller at the respective station, said laparoscopic tools matching in one to one correspondence with each other at the robotic surgery station and remote surgeon station and said laparoscopic tools being selectable via rotation of the turret based on surgery requirements.

2. The telerobotic surgery system according to claim 1, wherein said first and second controllers each include a force feedback module to provide haptic feedback to a user at the laparoscopic tool being manipulated.

3. The telerobotic surgery system according to claim 2, wherein said first and second controllers each include a variable force scaling module configured to modulate the haptic feedback to a user and increase or decrease the effective tool movement force felt by the user at the laparoscopic tool being manipulated.

4. The telerobotic surgery system according to claim 1, wherein said second controller is operative to effect movement of the second pair of robot arms and respective laparoscopic tools based on movement of said first pair of robot arms and laparoscopic tools.

5. The telerobotic surgery system according to claim 1, wherein said robotic surgery station includes at least one camera, wherein the harvested animal tissue is viewable by the at least one camera so that said at least one camera generates an actual animal tissue image and said remote surgeon station comprises at least one surgeon display cooperating with said at least one camera to display the actual animal tissue image.

6. The telerobotic surgery system according to claim 1, comprising at least one animating device coupled to said harvested animal tissue.

7. The telerobotic surgery system according to claim 6, wherein said at least one animating device simulates at least one of breathing, heartbeat, and blood perfusion.

8. The telerobotic surgery system according to claim 1, wherein said robotic surgery station is at a first location in a first structure at a first geographic point and said remote surgeon station is at a second location in a second structure at a second geographic point remote from the first geographic point.

9. A telerobotic surgery system for remote surgeon training, comprising:
 a robotic surgery station at a first location in a first structure at a first geographic point, and having a first pair of robot arms, each carrying a laparoscopic tool and each having a robot arm drive, and a first controller connected to each robot arm drive and controlling movement of the pair of robot arms and respective laparoscopic tool;
 harvested animated animal tissue at the robotic surgery station and comprising harvested animal tissue and at least one animating device coupled thereto;
 a remote surgeon station at a second location in a second structure at a second geographic point remote from the first geographic point, and having a second pair of robot arms, each carrying a laparoscopic tool and each having a robot arm drive, and a second controller connected to each robot arm drive at the remote surgeon station that receives data regarding movement of the second pair of robot arms and respective laparoscopic tool based on user manipulation of each laparoscopic tool at the remote surgeon station;
 a communications network coupling said first and second controllers, wherein the second controller at the robotic surgery station is operative as a master to communicate data to the first controller regarding user manipulation of the second pair of robot arms and respective laparoscopic tool, wherein the first controller is configured to control each robot arm drive and effect one-to-one movement of the first pair of robot arms and carried laparoscopic tools as a slave based on user manipulation of each laparoscopic tool at the remote surgeon station; and
 a left turret and right turret positioned at each of the robotic surgery station and remote surgeon station, each left and right turret supporting a plurality of robot arms, each robot arm having a laparoscopic tool and each having a robot arm drive and connected to the respective controller at the respective station, said laparoscopic tools matching in one to one correspondence with each other at the robotic surgery station and remote surgeon station and said laparoscopic tools being selectable via rotation of the turret based on surgery requirements.

10. The telerobotic surgery system according to claim 9, wherein said first and second controllers each include a force feedback module to provide haptic feedback to a user at the laparoscopic tool being manipulated.

11. The telerobotic surgery system according to claim 10, wherein said first and second controllers each include a variable force scaling module configured to modulate the haptic feedback to a user and increase or decrease the effective tool movement force felt by the user at the laparoscopic tool being manipulated.

12. The telerobotic surgery system according to claim 9, wherein said second controller is operative to effect movement of the second pair of robot arms and respective laparoscopic tools based on movement of said first pair of robot arms and laparoscopic tools.

13. The telerobotic surgery system according to claim 9, wherein said robotic surgery station includes at least one camera, wherein the harvested animated animal tissue is viewable by the at least one camera so that said at least one camera generates an actual animal tissue image and said remote surgeon station comprises at least one surgeon display cooperating with said at least one camera to display the actual animal tissue image.

14. The telerobotic surgery system according to claim 9, wherein said at least one animating device simulates at least one of breathing, heartbeat, and blood perfusion.

* * * * *